United States Patent
Scheiber

(10) Patent No.: US 11,491,177 B1
(45) Date of Patent: Nov. 8, 2022

(54) NONINVASIVE MEDICAL PROCEDURE FOR DESTRUCTION OF CANCER AND PRECANCEROUS CELLS

(71) Applicant: Lane Scheiber, Clearwater Beach, FL (US)

(72) Inventor: Lane Scheiber, Clearwater Beach, FL (US)

( * ) Notice: Subject to any disclaimer, the term of this patent is extended or adjusted under 35 U.S.C. 154(b) by 0 days.

(21) Appl. No.: 17/513,047

(22) Filed: Oct. 28, 2021

(51) Int. Cl.
*A61K 31/7105* (2006.01)
*C12N 15/113* (2010.01)
*A61K 9/127* (2006.01)
*A61P 35/00* (2006.01)

(52) U.S. Cl.
CPC ........ *A61K 31/7105* (2013.01); *A61K 9/1272* (2013.01); *A61P 35/00* (2018.01); *C12N 15/113* (2013.01)

(58) Field of Classification Search
CPC ............ C12N 15/1135; C12N 2310/11; C12N 2310/12; C12N 2310/14; C12N 2310/15
USPC ...... 412/9.1; 435/6.1, 91.1, 91.31, 455, 458; 514/44 R, 44 A; 536/23.1, 24.5
See application file for complete search history.

(56) References Cited

U.S. PATENT DOCUMENTS 9,522,114 B1   12/2016   Alcantar et al.

OTHER PUBLICATIONS

Aubrey, et al.. How does p53 induce apoptosis and how does this relate to p53-mediated tumour suppression? Cell Death & Differentiation. Nov. 17, 2017; 25:104-113; Hollstein, et al., p53 mutations in human cancers. Science. Jul. 5, 1991; 253(5015): 49-53.
Avci-Adali, et al., In vitro synthesis of modified mRNA for induction of protein expression in human cells. J Vis Exp. Nov. 13, 2014; (93):51943.
Baugh, et al., Why are there hotspot mutations in the TP53 gene in human cancers? Cell Death Diff. Jan. 2018; 25 (1):154-160.
Banerjee, 5'-teminal cap structure in eucaryotic messenger ribonucleic acids. Microbiol Rev. Jun. 1980; 44(2):175-205.
Dvir, et al., Deciphering the rules by which 5'-UTR sequences affect protein expression in yeast. Proc Natl Acad Sci USA Jul. 23, 2013; 110(30):e2792-2801.
Elbashir, et al., Duplexes of 21-nucleotide RNAs mediate RNA interference in cultured mammalian cells. Nature. May 24, 2001; 411(6836): 494-498.
Hamada, et al., Anionic complex with efficient expression and good safety profile for mRNA delivery. Pharmaceutics. Jan. 19, 2021; 13(1):126.
Hong, et al., Efficient tumor targeting of hydroxycamptothecin loaded PEGylated niosomes modified with transferrin. J Control Release. Jan. 19, 2009; 133(2):96-102.

Jayarama et al., Maximizing the potency of siRNA lipid nanoparticles for hepatic gene silencing in vivo, Angew Chern Int Ed Engl. Aug. 20, 2012, 51(34): 8529-8533.
Luanpitpong, et al., Selective cytotoxicity of single and dual anti-CD19 and anti-CD138 chimeric antigen receptor-natural killer cells against hematologic malignancies. J Immunol Res. Jul. 11, 2021; 2021: e5562630.
Maier et al., Biodegradable lipids enabling rapidly eliminated lipid nanoparticles for systemic delivery of RNAi therapeutics. Mol Ther. Aug. 2013; 21(8):1570-1578.
Nagata, et al., Synthesis and biological activity of artificial mRNA prepared with novel phosphorylating reagents. Nucleic Acids Res. Nov. 2010; 38(21):7845-7857.
Nichols, et al., Loss of heterozygosity of essential genes represents a widespread class of potential cancer vulnerabilities. Nat Commun. May 20, 2020; 11(1):2517.
Osada, et al., Polymeric micelles from poly(ethylene glycol)-poly(amino acid) block copolymer for drug and gene delivery. J R Soc Interface Jun. 6, 2009; 6(Suppl 3): S325-S339.
Pardi, et al., mRNA vaccines—a new era in vaccinology. Nat Rev Drug Discov. Apr. 2018; 17(4):261-279.
Patel, et al., Inhaled nanoformulated mRNA polyplexes for protein production in lung epithelium. Adv Mater. Feb. 2019;31(8):e1805116.
Qiu, et al., PEGylated KL4 peptide as an effective vector for mRNA delivery on lung epithelial cells. J Control Release. Nov. 28, 2019; 314:102-15.
Sabariegos, et al., Sequence homology required by human immunodeficiency virus type 1 to escape from short interfering RNAs. J Virol. Jan. 2006; 80(2):571-577.
Thess, et al., Sequence-engineered mRNA without chemical nucleoside modifications enables an effective protein therapy in large animals. Mol Ther. Sep. 2015; 23(9):1456-1464.
Wu, et al., Translation affects mRNA stability in a codon-dependent manner in human cells. Elife. Apr. 23, 2019; 8: e45396.
Zeng, et al., Highly branched poly(β-amino ester)s for gene delivery in hereditary skin diseases. Advanced Drug Del Rev. Sep. 2021; 176:113842.
Alexandrova, et al., p53 loss-of-heterozygosity is a necessary prerequisite for mutant p53 stabilization and gain-of-function in vivo. Cell Death Dis. Mar. 9, 2017; 8(3):e2661.
Alexandrova, et al., Improving survival by exploiting tumour dependence on stabilized mutant p53 for treatment. Nature. Jul. 16, 2015; 523(7560):352-6.
Almazov, et al., Use of p53 for therapy of human cancer. Mol Biol (Mosk). 2007; 21(6):947-63.
Grijalvo, et al., Cationic niosomes as non-viral vehicles for nucleic acids: challenges and opportunities in gene delivery. Pharmaceutics. Jan. 22, 2019; 11(2):50.

(Continued)

*Primary Examiner* — Jane J Zara
(74) *Attorney, Agent, or Firm* — Zagrebelsky Law P.A.; Robert Varkonyi

(57) ABSTRACT

Half of the cancers typically occur due to ineffective capability in their p53 proteins. The invention supplies the cells of the human body or patient with mRNA which will generate effective wild-type p53 proteins, so that this said protein can conduct proper surveillance inside the body's cells and act to destroy cells which have become or are about to become cancerous. The invention also includes introduction of interfering RNA to degrade mutated p53, allowing wild-type p53 proteins to form functional oligomers for cellular surveillance.

20 Claims, 1 Drawing Sheet

Specification includes a Sequence Listing.

(56) References Cited

OTHER PUBLICATIONS

Junttila, et al., Selective activation of p53-mediated tumor suppression in high-grade tumours. Nature. Nov. 25, 2010; 468(7323):567-571.

Klimovich, et al., Loss of p53 function at late states of tumorigenesis confers ARF-dependent vulnerability to p53 reactivation therapy. Proc Natl Acad Sci USA. Oct. 29, 2019; 116(44):22288-93.

Marie, et al., p53 signaling in cancer progression and therapy. Cancer Cell Int. Dec. 24, 2021; 21(1):703.

Martins, et al., Modeling the therapeutic efficacy of p53 restoration in tumors. Cell. Dec. 29, 2006; 127(7): 1323-1334.

Nakayama, et al., Intestinal cancer progression by mutant p53 through the acquisition of invasiveness associated with complex glandular formation. Oncogene. Oct. 19, 2017; 36(42):5885-5896.

Nobuta, et al., eIF4G-driven translation initiation of downstream ORFs in mammalian cells. Nucleic Acid Res. Oct. 9, 2020; 48(18):10441-55.

Qui, et al., PEGylated KL4 peptide as an effective vector for mRNA delivery on lung epithelial cells. J Control Release. Nov. 28, 2019; 314:102-115.

Solomon, et al., Mutant p53 gain of function underlies high expression levels of colorectal cancer stem cell markers. Oncogene. Mar. 2018; 37(12):1669-1684.

Uchida, et al., In vivo messenger RNA introduction into the central nervous system using polyplex nanomicelle. PLoS One. 2013; 8(2)e56220.

https://groups.molbiosci.northwestern.edu/holmgren/Glossary/Definitions/Def-D/downstream.html, last accessed Jun. 29, 2022.

https://www.genscript.com/biology-glossary/12162/UpstreamDownstream, last accessed Jun. 29, 2022.

http://www.informatics.jax.org/glossary/_5_utr, last accessed Jul. 11, 2022.

http://www.informatics.jax.org/glossary/_3_utr, last accessed Jul. 11, 2022.

SEQUENCE LISTING

<160> NUMBER OF SEQ ID NOS: 19

<210> SEQ ID NO 1
<211> LENGTH: 142
<212> TYPE: RNA
<213> ORGANISM: Homo sapiens

<400> SEQUENCE: 1
cucaaaaguc uagagccacc guccagggag cagguagcug cugggcuccg gggacacuuu      60
gcguucgggc ugggagcgug cuuuccacga cggugacacg cuucccugga uuggcagcca     120
gacugccuuc cggducacug cc                                              142

<210> SEQ ID NO 2
<211> LENGTH: 1182
<212> TYPE: RNA
<213> ORGANISM: Homo sapiens

<400> SEQUENCE: 2
auggaggagc cgcagucaga uccuagcguc gagcccccuc ugagucagga aacauuuuca      60
gaccuaugga aacuacuucc ugaaaacaac guucuguccc ccuugccguc ccaagcaaug     120
gaugauuuga ugcuguccccc ggacgauauu gaacaauggu ucacugaaga cccaggucca    180
gaugaagcuc ccagaaugcc agaggcugcu ccccccgugg ccccugcacc agcagcuccu     240
acaccggcgg ccccugcacc agcccccucc uggccccugu caucuucugu cccuucccag     300
aaaaccuacc agggcagcua cgguuuccgu cugggcuucu ugcauucugg gacagccaag     360
ucugugacuu gcacguacuc cccugcccuc aacaagaugu uugccaacu ggccaagacc      420 ugcccugugc agcugugggu ugauuccaca ccccgcccg gcacccgcgu ccgcgccaug      480
gccaucuaca gcagucaca gcacaugacg gagguuguga ggcgcugccc ccaccaugag     540
cgcugcucag auagcgaugg ucuggccccu ccucagcauc uuauccgagu ggaaggaaau     600
uugcgugugg aguauuugga ugacagaaac acuuuucgac auagugugugu ggugcccuau   660 gagccgccug agguuggcuc ugacuguacc accauccacu acaacuacau guguaacagu    720
uccugcaugg gcggcaugaa ccggaggccc auccucacca ucaucacacu ggaagacucc    780
agugguaauc uacugggacg gaacagcuuu gaggugcgug uuugugccug uccugggaga    840
gaccggcgca cagaggaaga gaaucuccgc aagaaagggg agccucacca cgagcugccc    900
ccagggagca cuaagcgagc acugcccaac aacaccagcu ccucucccca gccaaagaag    960
aaaccacugg auggagaaua uuucacccuu cagauccgug ggcugagcg cuucgagaug    1020 uuccgagagc ugaaugaggc cuuggaacuc aaggaugccc aggcugggaa ggagccaggg   1080
gggagcaggg cucacuccag ccaccugaag uccaaaaagg gucagucuac cucccgccau  1140
aaaaaacuca guucaagac agaagggccu gacucagacu ga                       1182

<210> SEQ ID NO 3
<211> LENGTH: 1182
<212> TYPE: RNA
<213> ORGANISM: artificial sequence
<220> FEATURE:
<223> OTHER INFORMATION: modified p53 sequence from H sapiens

<400> SEQUENCE: 3
auggaggagc cgcagucaga ucccagcguc gagccccccc ugagucagga gacguucuca      60
gaccuaugga aacuacuccc cgagaacaac gugcuguccc ccuugccguc ccaagcaaug     120
gaugauuuga ugcuguccccc ggacgauauu gagcaauggu ucacggagga cccaggucca   180

-continued

```
gaugaggcuc ccagaaugcc agaggcugcu cccccgugg ccccgcacc agcagcuccc      240 acgccggcgg cccccgcacc agcccccucc uggcccugu caucuucugu ccccucccag      300
aaaaccuacc agggcagcua cgguuuccgg cugggcuucu ugcauucugg acggccaag      360 ucugugacgu gcacguacuc ccccgcccuc aacaagaugu ucugcaacu ggccaagacc       420 ugccccgugc agcuguggu ggauuccacg cccccgcccg cacccgcgu ccgcgccaug        480 gccaucuaca agcagucaca gcacaugacg gaggugguga ggcgcugccc ccaccaugag      540
cgcugcucag auagcgaugg ucuggccccc cccagcauc ucauccgagu ggagggaaac      600
uugcggugug aguacuugga ugacagaaac acguuccgac auagguggu ggugcccuac      660 gagccgcccg aggugggcuc ugacuguacc accauccacu acaacuacau guguaacagu    720
uccugcaugg gcggcaugaa ccggaggccc auccucacca ucaucacgcu ggaggacucc    780 aggguaacc uacugggacg aacagcuuc gaggugcggg ugugugccug ucccgggaga      840
gaccggcgca cggaggagga gaaccuccgc aagaaagggg agccccacca cgagcugccc    900
ccagggagca cgaagcgagc acugcccaac aacaccagcu ccucuccca gccaaagaag     960 aaaccacugg auggagagua cuucacccuc cagauccggg ggcggagcg cuucgagaug    1020 uuccgagagc ugaacgaggc cuuggagcuc aaggaugccc aggcugggaa ggagccaggg    1080
gggagcaggg cucacuccag ccaccugaag uccaaaaagg gucagucuac cucccgccau    1140
aaaaaacuca uguucaagac ggagggccc gacucagacu ga                         1182
```

<210> SEQ ID NO 4
<211> LENGTH: 1182
<212> TYPE: RNA
<213> ORGANISM: artificial sequence
<220> FEATURE:
<223> OTHER INFORMATION: modified p53 sequence from H sapiens

<400> SEQUENCE: 4

```
auggaggagc cgcagucaga ucccagcguc gagcccccc ugagucagga gaccuucuca       60
gaccuaugga aacuacugcc cgagaacaac guccugucc ccuugccguc ccaagcaaug      120
gaugauuuga ugcugucccc ggacgauauu gagcaauggu ucaccgagga cccagguccca   180 gaugaggcuc ccagaaugcc agaggcugcu cccccgugg ccccgcacc agcagcuccc      240 accccggcgg cccccgcacc agcccccucc uggcccugu caucuucugu ccccucccag      300
aaaaccuacc agggcagcua cgguuuccgg cugggcuucu ugcauucugg acggccaag      360 ucugugaccu gcacguacuc ccccgcccuc aacaagaugu ucugcaacu ggccaagacc       420 ugccccgugc agcuguggu cgauuccacc cccccgcccg cacccgcgu ccgcgccaug        480 gccaucuaca agcagucaca gcacaugacg gaggucguga ggcgcugccc ccaccaugag      540
cgcugcucag auagcgaugg ucuggccccc cccagcauc ugauccgagu ggagggaaac      600
uugcggugug aguacuugga ugacagaaac accuuccgac auagguggu ggugcccuac      660 gagccgcccg aggucggcuc ugacuguacc accauccacu acaacuacau guguaacagu    720
uccugcaugg gcggcaugaa ccggaggccc auccucacca ucauccccu ggaggacucc     780 aggguaacc uacugggacg aacagcuuc gaggugcggg ucugugccug ucccgggaga      840
gaccggcgca cggaggagga gaaccuccgc aagaaagggg agccccacca cgagcugccc    900
ccagggagca ccaagcgagc acugcccaac aacaccagcu ccucuccca gccaaagaag    960 aaaccacugg auggagagua cuucacccug cagauccggg ggcggagcg cuucgagaug    1020
```

```
uuccgagagc ugaacgaggc cuuggagcuc aaggaugccc aggcugggaa ggagccaggg    1080
gggagcaggg cucacuccag ccaccugaag uccaaaaagg gucagucuac cucccgccau    1140
aaaaaacuca uguucaagac cgaggggccc gacucagacu ga                      1182
```

```
<210> SEQ ID NO 5
<211> LENGTH: 1188
<212> TYPE: RNA
<213> ORGANISM: Homo sapiens

<400> SEQUENCE: 5
cauucuccac uucuuguucc ccacugacag ccucccaccc ccaucucucc cuccccugcc     60 auuuugggu uugggucuuu gaacccuugc uugcaauagg ugugcgucag aagcacccag    120
gacuuccauu ugcuuugucc cggggcucca cugaacaagu uggccugcac ugguguuuug    180
uuguggggag gaggauggggg aguaggacau accagcuuag auuuuaaggu uuuuacgugug  240 agggauguuu gggagaugua agaaauguuc uugcaguuaa ggguuaguuu acaaucagcc    300
acauucuagg uaggggccca cuucaccgua cuaaccaggg aagcuguccc ucacuguuga    360
auuuucucua acuucaaggc ccauaucugu gaaaugcugg cauuugcacc uaccucacag    420
agugcauugu gagggguuaau gaaauaaugu acaucuggcc uugaaaccac cuuuuauuac   480 augggguccua gaacuugacc cccuugaggg ugcuuguucc cucucccugu ggucggugg    540 guugguaguu ucuacaguug ggcagcuggu uaggagagg gaguugucaa gucucugcu     600 gcccagccaa acccugucug acaaccucuu ggugaaccuu aguaccuaaa aggaaaucuc    660
accccauccc acacccugga ggauuucauc ucuuguauau gaugaucugg auccaccaag   720 acuuguuua ugcucagggu caauuucuuu uucuuuuuu uuuuuuuuu uucuuuuucu      780 uugagacugg gucucgcuuu guugcccagg cuggagugga guggcugau cuuggcuuac    840 ugcagccuuu gccucccgg cucgagcagu ccugccucag ccuccggagu agcugggacc    900
acagguucau gccaccaugg ccagccaacu uuugcauguu uuguagagau ggggucucac    960 agguugccc aggcuggucu caaacccug ggcucaggcg auccaccugu cucagccucc    1020
cagagugcug ggauuacaau uguagagccac cacguccagc uggaagggguc aacaucuuuu  1080 acauucugca agcacaucug cauuuucacc ccacccuucc ccuccuucuc ccuuuuuaua    1140
ucccauuuuu auaucgaucu cuuauuuuac aauaaaacuu ugcugcca                1188
```

```
<210> SEQ ID NO 6
<211> LENGTH: 21
<212> TYPE: RNA
<213> ORGANISM: artificial sequence
<220> FEATURE:
<223> OTHER INFORMATION: siRNA target from H sapiens p53 mutation

<400> SEQUENCE: 6
guugugaggc acugccccca c                                               21
```

```
<210> SEQ ID NO 7
<211> LENGTH: 21
<212> TYPE: RNA
<213> ORGANISM: artificial sequence
<220> FEATURE:
<223> OTHER INFORMATION: siRNA target from H sapiens p53 mutation

<400> SEQUENCE: 7
uccugcauga gcggcaugaa c                                               21
```

```
<210> SEQ ID NO 8
<211> LENGTH: 21
<212> TYPE: RNA
<213> ORGANISM: artificial sequence
<220> FEATURE:
<223> OTHER INFORMATION: siRNA target sequence from H sapiens p53
      mutation

<400> SEQUENCE: 8
ggcaugaacc agaggcccau c                                            21

<210> SEQ ID NO 9
<211> LENGTH: 21
<212> TYPE: RNA
<213> ORGANISM: artificial sequence
<220> FEATURE:
<223> OTHER INFORMATION: siRNA target sequence from H sapiens p53
      mutation

<400> SEQUENCE: 9
ggcaugaacu ggaggcccau c                                            21

<210> SEQ ID NO 10
<211> LENGTH: 21
<212> TYPE: RNA
<213> ORGANISM: artificial sequence
<220> FEATURE:
<223> OTHER INFORMATION: siRNA target sequence from H sapiens p53
      mutation

<400> SEQUENCE: 10
augaaccgga gccccauccu c                                            21

<210> SEQ ID NO 11
<211> LENGTH: 21
<212> TYPE: RNA
<213> ORGANISM: artificial sequence
<220> FEATURE:
<223> OTHER INFORMATION: siRNA target sequence from H sapiens p53
      mutation

<400> SEQUENCE: 11
uuugaggugc auguuugugc c                                            21

<210> SEQ ID NO 12
<211> LENGTH: 21
<212> TYPE: RNA
<213> ORGANISM: artificial sequence
<220> FEATURE:
<223> OTHER INFORMATION: siRNA target sequence from H sapiens p53
      mutation

<400> SEQUENCE: 12
uuugaggugu guguuugugc c                                            21

<210> SEQ ID NO 13
<211> LENGTH: 21
<212> TYPE: RNA
<213> ORGANISM: artificial sequence
<220> FEATURE:
<223> OTHER INFORMATION: siRNA target sequence from H sapiens p53
      mutation

<400> SEQUENCE: 13
gggagagacu ggcgcacaga g                                            21

<210> SEQ ID NO 14
```

-continued

```
<211> LENGTH: 21
<212> TYPE: RNA
<213> ORGANISM: artificial sequence
<220> FEATURE:
<223> OTHER INFORMATION: siRNA target sequence from H sapiens p53
      mutation

<400> SEQUENCE: 14
gugaggcgcu accccccacca u                                              21

<210> SEQ ID NO 15
<211> LENGTH: 21
<212> TYPE: RNA
<213> ORGANISM: artificial sequence
<220> FEATURE:
<223> OTHER INFORMATION: siRNA target sequence from H sapiens p53
      mutation

<400> SEQUENCE: 15
aagauguuuu accaacuggc c                                               21

<210> SEQ ID NO 16
<211> LENGTH: 21
<212> TYPE: RNA
<213> ORGANISM: artificial sequence
<220> FEATURE:
<223> OTHER INFORMATION: siRNA target sequence from H sapiens p53
      mutation

<400> SEQUENCE: 16
aacuacaugu auaacaguuc c                                               21

<210> SEQ ID NO 17
<211> LENGTH: 21
<212> TYPE: RNA
<213> ORGANISM: artificial sequence
<220> FEATURE:
<223> OTHER INFORMATION: siRNA target sequence from H sapiens p53
      mutation

<400> SEQUENCE: 17
ugugccuguc uugggagaga c                                               21

<210> SEQ ID NO 18
<211> LENGTH: 21
<212> TYPE: RNA
<213> ORGANISM: artificial sequence
<220> FEATURE:
<223> OTHER INFORMATION: siRNA target sequence from H sapiens p53
      mutation

<400> SEQUENCE: 18
gugcguguuu augccugucc u                                               21

<210> SEQ ID NO 19
<211> LENGTH: 21
<212> TYPE: RNA
<213> ORGANISM: artificial sequence
<220> FEATURE:
<223> OTHER INFORMATION: siRNA target sequence from H sapiens p53
      mutation

<400> SEQUENCE: 19
aaucuacugc gacggaacag c                                               21
```

NONINVASIVE MEDICAL PROCEDURE FOR DESTRUCTION OF CANCER AND PRECANCEROUS CELLS

FIELD OF INVENTION

This invention relates to methods of treating cancer. Specifically, the invention provides procedures for destroying cancerous and precancerous cells using p53.

BACKGROUND THE OF INVENTION

Approximately half of all human cancers possess mutations in the tumor suppressor gene TP53. Mutations in the p53 protein include loss of function mutations, typically via point mutations in the DNA binding domain, and gain of function mutations due to improper DNA binding. During the oncogenic process, a loss of function mutant p53 commonly gains increased expression, followed by either deletion of the other TP53 gene or replacement of the wild-type TP53 by the mutant TP53 allele. (Aubrey, et al., How does p53 induce apoptosis and how does this relate to p53-mediated tumour suppression? Cell Death & Differentiation. 2017 Nov. 17; 25:104-113; Hollstein, et al., p53 mutations in human cancers. Science. 1991 Jul. 5; 253(5015): 49-53).

The p53 protein is a 53 kDa polypeptide located on chromosome 17 that regulates the DNA transcription of around 500 proteins that include proteins involved in cell cycle arrest, cell senescence, DNA repair, metabolic adaptation and apoptosis. (Kastenhuber & Lowe, Putting p53 in context. Cell. 2017 Sep. 7; 170(6): 1062-1078; Laptenko & Prives, Transcriptional regulation by p53: one protein, many possibilities. Cell Death Differ. 2006; 13: 951-961; Aubrey, et al., How does p53 induce apoptosis and how does this relate to p53-mediated tumour suppression?Cell Death & Differentiation. 2017 Nov. 17; 25:104-113). p53 contains two N-terminal transactivation domains with a central DNA binding domain and C-terminal nuclear localization domain, and forms a homotetramer resulting in transcriptional activity. (Riley, et al., Transcriptional control of human p53-regulated genes. Nat Rev Mol Cell Biol. 2008 May; 9(5): 402-412; Kamada, et al., Tetramer formation of tumor suppressor protein p53: structure, function, and applications. Biopolymers. 2016 Nov. 4; 106(4): 598-612; Laptenko & Prives. Transcriptional regulation by p53: one protein, many possibilities. Cell Death Differ. 2006; 13: 951-961). p53 stimulates synthesis of p21, which in turn complexes with cyclin-dependent kinase 2 (cdk2), a cell division-stimulating protein, resulting in inhibition of cdk2 and arrest of the cell cycle in G1/S. (Abbas & Dutta. p21 in cancer: intricate networks and multiple activities. Nat Rev Cancer. 2009 June; 9(6): 400-414). Additionally, p53 targets the transcription of Puma, also called Bcl-2-binding component 3 (BBC3), NOXA, also called phorbol-12-myristate-13-acetate-induced protein-1 (PMAIP1), BTG family member 2 (BTG2; also called NGF-inducible anti-proliferative protein), which are pro-apoptotic genes, and microRNAs, such as miR-34. (Oda, et al., Noxa, a BH3-only member of the bcl-2 family and candidate mediator of p53-induced apoptosis. Science. 2000 May 12; 288(5468):1053-1058; Yu, et al., PUMA induces the rapid apoptosis of colorectal cancer cells. Mol Cell. 2001 March; 7(3):673-682; Han, et al., Expression of bbc3, a pro-apoptotic BH3-only gene, is regulated by diverse cell death and survival signals. Pro Natl Acad Sci USA. 2001 Sep. 25; 98(20):11318-11323; Villunger, et al., p53- and drug-induced apoptotic responses mediated by BH3-only proteins puma and noxa. Science. 2003 Nov. 7; 302(5647):1036-1038; Jeffers, et al., Puma is an essential mediator of p53-dependent and -independent apoptotic pathways. Cancer Cell. 2003 October; 4(4):321-328; Allen, et al., Global analysis of p53-regulated transcription identifies its direct targets and unexpected regulatory mechanisms. Elife. 2014 May 27; 3:e02200; He, et al., A microRNA component of the p53 tumour suppressor network. Nature. 2007 Jun. 28; 447(7148):1130-1134). p53 also incudes other cell division proteins, such as the serine/threonine-protein kinase, polo-like kinase 2 (PLK2). (Allen, et al., Global analysis of p53-regulated transcription identifies its direct targets and unexpected regulatory mechanisms. Elife. 2014 May 27; 3:e02200).

p53 is degraded via proteasomal enzyme MDM2, an E3 ligase, which forms a negative feedback loop with p53. (Haupt, et al., Mdm2 promotes the rapid degradation of p53. Nature. 1997 May 15; 387(6630): 296-299; Kubbutat, et al., Regulation of p53 stability by Mdm2. Nature. 1997 May 15; 387(6630): 299-303; Michael & Oren, The p53 and Mdm2 families in cancer. Curr Opin Genetics Dev. 2002 February; 12(1); 53-59). DNA damage or oncogene activation caused p53 protein levels to increase, due to Mdm2 is inhibition and acetylation and phosphorylation of p53. (Vousden & Lane, p53 in health and disease. Nat Rev Mol Cell Biol. 2007 April; 8(4): 275-283; Oren, Regulation of the p53 tumor suppressor protein. J Biol Chem. 1999 Dec. 17; 274(51): 36031-36034).

p53-induced apoptosis operates through two pathways. The first is the BCL-regulated pathway, activated by stress, such as endoplasmic reticulum stress, DNA damage, or cytokine deficiency. BH3-only proteins, such as BIM, PUMA, BID, BMF, BAD, NOXA and others, inhibit pro-survival BCL-2 proteins, like BCL-2, BCL-XL, MCL-1, allowing release of certain apoptotic proteins. (Ke, et al., BCL-2 family member BOK is widely expressed but its loss has only minimal impact in mice. Cell Death Differ. 2012 June; 19(6):915-925; Ke, et al., Impact of the combined loss of BOK, BAX and BAK on the hematopoietic system is slightly more severe than compound loss of BOX and BAK. Cell Death Dis. 2015 Oct. 22; 6(10): e1938; Llambi, et a., BOK is a non-canonical BCL-2 family effector of apoptosis regulated by ER-associated degradation. Cell. 2016 Apr. 7; 165(2):421-433). Some of these proteins are transcriptionally regulated by p53, such as BAX and APF-1. (Selvakumaran, et al., Immediate early up-regulation of bax expression by p53 but not TGFb1: a paradigm for distinct apoptotic pathways. Oncogene. 1994 June; 9(6):1791-1798; Thornborrow, et al., A conserved intronic response element mediates direct p53-dependent transcriptional activation of both the human and murine bax genes. Oncogene. 2002 Feb. 7; 21(7):990-999; Robles, et al., APAF-1 is a transcriptional target of p53 in DNA damage-induced apoptosis. Cancer Res. 2001 Sep. 15; 61(18):6660-6664). BAX activation results in permeabilization of the mitochondrial membrane. The second apoptosis pathway is the extrinsic pathway, which is activated by tumor necrosis factor receptors (TNFR). (Strasser, et al., Bcl-2 and Fas/APO-1 regulate distinct pathways to lymphocyte apoptosis. EMBO J. 1995 Dec. 15; 14(24):6136-6147; Green, et al., Apoptotic pathways: ten minutes to dead. Cell. 2005 Jun. 3; 121(5):671-674; Czabotar, et al., Control of apoptosis by the BCL-2 protein family: implications for physiology and therapy. Nat Rev Mol Cell Biol. 2014 January; 15(1):49-63). Fas-associated protein with death domain (FADD) and TRADD complexation at the membrane receptors activate caspases, like caspase-8 and caspases 3 and 7, cascading to induce apoptosis, which includes the BCL-2 pathway in certain cells. (Varfolomeev, et al., Targeted disruption of the mouse Caspase 8 gene ablates cell death induction by the TNF receptors, Fas/Apo1, and DR3 and is lethal prenatally. Immunity. 1998 August; 9(2):267-276; Strasser, et al., The many roles of FAS receptor signaling in the immune system. Immunity. 2009 Feb. 20; 30(2):180-192; Scaffidi, et al., Two CD95 (APO-1/Fas) signaling pathways. EMBO J. 1998 Mar. 16; 17(6):1675-1687; Li, et al., Cleavage of BID by caspase 8 mediates the mitochondrial damage in the Fas pathway of apoptosis. Cell. 1998 Aug. 21; 94(4):491-501; Luo, et al., Bid, a Bcl-2 interacting protein, mediates cytochrome c release from mitochondria in response to activation of cell surface death receptors. Cell. 1998 Aug. 21; 94(4):481-490).

Mutations in p53, typically through missense point mutations, can result in loss of function or gain of function changes in the resulting protein. (Brosh & Rotter, When mutations gain new powers: news from the mutant p53 field. Nat Rev Cancer. 2009 October; 9(10):701-713; Muller, et al., Mutant p53 in cancer: new functions and therapeutic opportunities. Cancer Cell. 2014 Mar. 17; 25(3):304-317). Loss of function mutations are common in cancer, whereby p53 protein possesses altered efficiency that ranges from reduced efficiency to complete loss of function. (Freed-Pastor, et al., Mutant p53 disrupts mammary tissue architecture via the mevalonate pathway. Cell. 2012 Jan. 20; 148(1-2):244-258; Nakayama, et al., Intestinal cancer progression by mutant p53 through the acquisition of invasiveness associated with complex glandular formation. Oncogene. 2017 Oct. 19; 36(42):5885-5896; Alexandrova, et al., p53 loss of heterozygosity is a necessary prerequisite for mutant p53 stabilization and gain-of-function in vivo. Cell Death Dis. 2017 Mar. 9; 8(3):e2661). Due to the functional complexation of p53, i.e. the formation of p53 tetramers, mutant p53 can also exert dominant negative effects (DNE) further eliminating the functionality of wild-type p53 in the cells during early neoplastic transformation (Vousden & Lane, p53 in health and disease. Nat Rev Mol Cell Biol. 2007 April; 8(4):275-283; and Freed-Pastor & Prives, Mutant p53: one name, many proteins. Genes Dev. 2012 Jun. 15; 26(12):1286-1286). Furthermore, wild-type p53 has been found to stabilize mutant p53 and increase nuclear localization. (Nakayama, et al., Intestinal cancer progression by mutant p53 through the acquisition of invasiveness associated with complex glandular formation. Oncogene. 2017 Oct. 19; 36(42):5885-5896; Alexandrova, et al., p53 loss of heterozygosity is a necessary prerequisite for mutant p53 stabilization and gain-of-function in vivo. Cell Death Dis. 2017 Mar. 9; 8(3):e2661). Gain of function mutant p53 is found in numerous cancers, including metastatic cancers and increases invasiveness. (Morton, et al., Mutant p53 drives metastasis and overcomes growth arrest/senescence in pancreatic cancer. Proc Natl Acad Sci USA. 2010 Jan. 5; 107(1):246-251; Nakayama, et al., Intestinal cancer progression by mutant p53 through the acquisition of invasiveness associated with complex glandular formation. Oncogene. 2017 Oct. 19; 36(42):5885-5896; Nakayama & Oshima, Mutant p53 in colon cancer. J Mol Cell Biol. 2019 Apr. 1; 11(4): 267-276).

Treatment by elimination of mutant p53 reduced tumor progression, suggesting mutant p53 maintains tumor growth. (Alexandrova, et al., Improving survival by exploiting tumor dependence on stabilized mutant p53 for treatment. Nature. 2015. 2015 Jul. 16; 523(7560):352-356; Solomon, et al., Mutant p53 gain of function underlies high expression levels of colorectal cancer stem cell markers. Oncogene. 2018 March; 37(12):1669-1684). Further, reestablishment of wild-type p53 in gastrointestinal or hematopoietic cancers, where p53 loss was linked in part to oncogenesis, resulted in apoptosis, while solid organ cancers treated to establish wild-type p53 resulted in senescence. (Martins, et al., Modeling the therapeutic efficacy of p53 restoration in tumors. Cell. 2006 Dec. 29; 127(7): 1323-1334; Junttila, et al., Selective activation of p53-mediated tumor suppression in high-grade tumours. Nature. 2010 Nov. 25; 468(7323):567-571; Merritt, et al., The role of p53 in spontaneous and radiation-induced apoptosis in the gastrointestinal tract of normal and p53-deficient mice. Cancer Res. 1994 Feb. 1; 54(3):614-617; Clarke, et al., Thymocyte apoptosis induced by p53-dependent and independent pathways. Nature. 1993 Apr. 29; 362(6423):849-852).

However, in vivo treatments have not been established as of yet. Exogenous mRNA cannot be administered directly to a patient, as such mRNA is immunostimulatory, resulting in a strong immune response. (Pardi, et al., mRNA vaccines—a new era in vaccinology. Nat Rev Drug Discov. 2018 April; 17(4):261-279; Chen, et al., RNA sensors of the innate immune system and their detection of pathogens. IUBMB Life. 2017 May; 69(5): 297-304). Further, mRNAs must be protected from endogenous RNases that would degrade the nucleic acids. (Kauffman, et al., Materials for non-viral intracellular delivery of messenger RNA therapeutics. J Control Release. 2016 Oct. 28; 240:227-234; Midoux & Pichon, Lipid-based mRNA vaccine delivery systems. Expert Rev Vaccines. 2015 February; 14(2):221-234).

SUMMARY OF THE INVENTION

The industry currently uses introduction of protein to treat medical conditions where deficiencies are the cause of such medical disorders, such as insulin provided to diabetics to manage high blood sugar or adalimumab, a monoclonal antibody that works by inactivating tumor necrosis factor-alpha (TNFα), to manage inflammatory arthritis.

This present invention administers mRNA to introduce wild-type p53 protein to cells to reinstate cell surveillance of the protein in cancerous or precancerous cells, and induce destruction of those cells. Introduction of the mRNA can be efficiently undertaken using carrier molecules that protect the mRNA and enhance uptake and translation. (Kauffman, et al., Materials for non-viral intracellular delivery of messenger RNA therapeutics. J Control Release. 2016 Oct. 28; 240:227-234; Guan & Rosenecker, Nanotechnologies in delivery of mRNA therapeutics using nonviral vector-based delivery systems. Gene Ther. 2017 Jan. 17; 24:133-143). Naked RNA is subject to RNases (Tsui, et al., Stability of endogenous and added RNA in blood specimens, serum, and plasma. Clin Chem. 2002 October; 48(10):1647-1653). The method includes contacting a cell with a composition comprising a carrier and at least one ribonucleic acid disposed in the carrier. The cell is cancerous or precancerous, and the mRNA induce senescence or apoptosis in the cell. In certain variations of the invention, the mRNA is administered into a patient resulting in the cell contacting the composition. In such embodiments, the patient has a cancerous or precancerous growth. Examples of administration to a patient includes, without limiting the scope of the invention, by aerosol administration, inhalation administration, intratumoral injection, intraarterial injection, or intravenous injection. Alternatively, the invention provides a method of treating cancer or precancer in a patent by administering a therapeutically effective amount of the compositions disclosed herein.

In certain embodiments, the carrier can be a microvesicle, polyplex nanomicelle, PEGylated synthetic KL4 peptide, hyperbranched poly (beta amino esters), or a mRNA-polyethylenimine complex. The carrier optionally also includes a targeting molecule on the surface of the carrier, allowing the carrier to interface with cancerous or precancerous cells expressing the conjugate ligand or molecule. The targeting molecule can be anti-alpha fetoprotein, anti-bladder tumor antigen, anti-BRCA1, anti-BRCA2, anti-beta 2 microglobulin HRP, anti-mucin 16, anti-CD10, anti-CD107a, anti-CD13, anti-CD 15, anti-CD 19, anti-CD 20, anti-CD 22, anti-CD 25, anti-CD 117, anti-CD138, anti-CD146, anti-CD147, anti-CD227, CD318, anti-CD326, anti-CD66, anti-CD56, anti-carcinoembryonic antigen, chlorotoxin, anti-epithelial tumor antigen, anti-melanoma-associated antigen, anti-cancer/testis antigen 1B, anti-transferrin, somatostatin receptor ligand, arginulglycylaspartic acid peptide, epidermal growth factor, and combinations thereof. Optionally, the target molecule or molecules is selected based on a biopsy, and identification of specific cancer markers within a patient.

Where the carrier is a microvesicle, the microvesicle optionally includes an interior space. Non-limiting examples of microvesicles are a niosome, liposome, or lipid nanoparticle. Where the carrier is a noisome, the noisome optionally includes a hydrophobic bilayer defining an aqueous interior space, and a bilayer optionally formed of at least one surfactant, at least one negative charged molecule and at least one cholesterol. The surfactant or surfactants optionally include crown ether amphiphiles bearing a steroidal moiety, 1,2-dialkyl glycerol polyoxyethylene ether, hexadecyl poly-5-oxyethylene ether, hexadecyl poly-5-oxyethylene ether ($C_{16}EO_5$); octadecyl poly-5-oxyethylene ether ($C_{18}EO_5$); hexadecyl diglycerol ether ($C_{16}G_2$); sorbitan monopalmitate, sorbitan monostearate, poly-24-oxyethylene cholesteryl ether, polysorbate 20, Span detergents, Brij detergents, polyoxyethylene, and polysorbates. The one or more negative charged molecules optionally are polyoxyethylene (61), sorbitan monostearate, cetyl sulphate, phosphatidic acid, phosphatidyl serine, oleic acid, palmitic acid, and/or dicetyl phosphates. In specific variations, the niosome bilayer comprises sorbitan monostearate, at least one cholesterol, and dicetyl phosphate at a ratio of 1:1:0.1 (surfactant: cholesterol: negative charged molecule).

Where the carrier is a a hyperbranched poly (beta amino esters), the carrier is formed of linear poly(beta amino esters) end-capped with a trifunctional amine, such as N-methyl 1,3 diaminopropane. Where the carrier is mRNA-polyethylenimine complex, the carrier is formed of polyethyleneimine (PEI) compounds that have the ability to complex with RNA, such as poly(amido ethylenimine); and poly(ethylene imine). Optionally the carrier also includes poly(phosphoramidates); poly(phosphazenes); poly(dimethylaminoethyl methacrylate); 3-imidazol-1-yl-propionic acid ester of hydroxyethyl methacrylate; poly(phosphoesters); poly(N-2-hydroxypropyl methacrylamide); dimethylaminoethyl; 1-methyl-2-piperidine methanol; N,N-diethylaminoethanol; dimethyl 3,3'-dithiobispropionimidate; poly(4-hydroxy-L-proline ester); poly(γ-(4-aminobutyl)-L-glycolic acid); poly(ethylene glycol); poly(L-lysine); and/or dithiobis (succinimidylpropionate). The carrier optionally includes theoretical charge ratios. The charge ratio of mRNA:PEI can vary from 1:6 to 1:14. Nonlimiting examples include 1:6, 1:7, 1:8, 1:9. 1:10, 1:11, 1:12, 1:13, or 1:14. Additionally, the charge ratios of mRNA to γ-PGA can vary from 1:4 to 1:12. Nonlimiting examples include 1:4, 1:5, 1:6, 1:7, 1:8, 1:9. 1:10, 1:11, or 1:12. The carrier optionally includes theoretical charge ratios of 1:8:4 (mRNA: PEI: γ-polyglutamic acid) to 1:8:12 (mRNA/PEI/γ-PGA). Very useful charge ratios are 1:8:6, 1:8:7, 1:8:8, 1:8:9, or 1:8:10. However, any combination of charge ratios mRNA:PEI and mRNA to γ-PGA can be used to form charge ratios of mRNA: PEI: γ-PGA). For example, without limiting the scope of the invention, the charge ratios of mRNA: PEI: γ-PGA can be 1:6:4, 1:7:4, 1:14:4, 1:6:5:1:7:5, 1:14:5, 1:6:12, 1:7:12, 1:14:12, or similar charge ratios selected from the above. Where the carrier is a polyplex nanomicelle, the carrier is polyethylene glycol-polyamino acid block copolymer.

The at least one ribonucleic acid includes a 5'-untranslated region of messenger ribonucleic acid (UTR), p53 messenger ribonucleic acid disposed downstream of the 5'-UTR, and a 3'-untranslated region (UTR) disposed downstream of the p53 messenger ribonucleic acid. A poly A is attached to the 3'-UTR. In specific variations of the invention, the 5'-UTR is from HSD17B4 (hydroxysteroid (17-β) dehydrogenase 4), and optionally is SEQ ID No. 1. The 5'-UTR optionally includes a 5' cap analog, such as 7mG(5')ppp(5')N₁pNp, where $N_i$ is a nucleotide and Np is the 5' end of a nucleic acid. (See, Banerjee, 5'terminal cap structure in eucaryotic messenger ribonucleic acids. Microbiol Rev. 1980 June; 44(2):175-205). Specific variations of the p53 messenger ribonucleic acid are SEQ ID No. 2, 3, or 4. Specific variation of the 3'-UTR is from albumin, and optionally is SEQ ID No. 5.

The composition optionally includes at least one interfering RNA. The interfering RNA is a dsRNA, siRNA or shRNA directed against a host cell's mutated p53 mRNA. The mutated p53 mRNA can be identified from a biopsy of a patient, or can be directed toward one or more common p53 mutations. Where the interfering RNA is dsRNA molecules comprising 16-23 nucleotides, e.g., 16, 17, 18, 19, 20, 21, 22, 23, 24, or 25 nucleotides, in each strand. The two strands are substantially identical, e.g., at least 95% (or more, e.g. 5%, 90%, 95%, or 100%) identical. The interfering RNA is optionally fully complementary, or has 1 or 2 mismatches, outside the target central coding section. The interfering RNA includes 21-23 nucleotides per strand. Optional siRNA molecules are complementary to the sequences found in SEQ ID. Nos. 67, 8, 9, 10, 11, 12, 13, 14, 15, 16, 17, 18, 19, or combinations thereof.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1A:
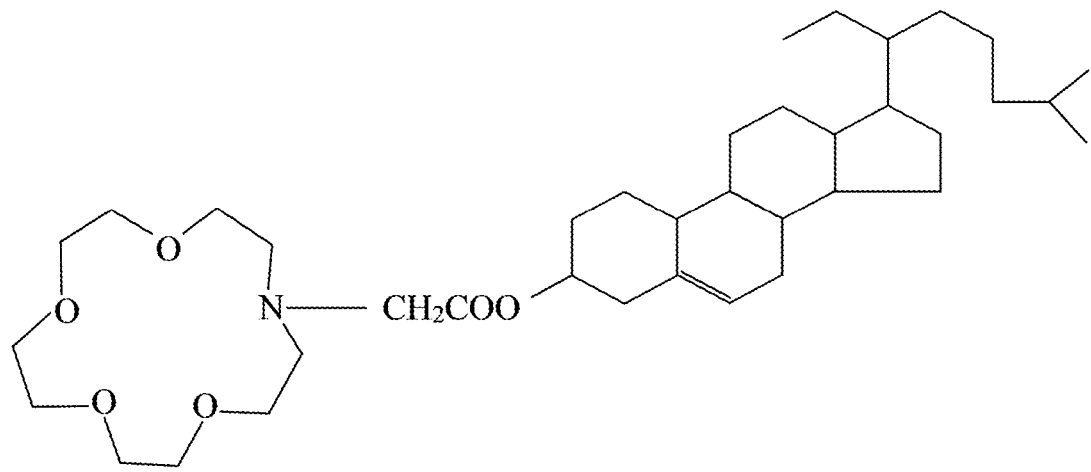
FIG. 1(a) is a structural formula of an exemplary crown ether for an embodiment of the carrier.

The inventive composition is designed to introduce wild-type p53 (wt p53) into cancerous or precancerous cells. The invention uses messenger ribonucleic acid (mRNA) comprising a 5' untranslated region (UTR), an open reading frame encoding a wild-type p53 protein, a 3' end UTR and a poly(A) tail where the code for a wild-type p53 protein is like that obtained from a fully functional TP53 gene. An mRNA so constructed is referred to as a wild-type p53 mRNA. It may also be modified as described below.

As used herein, the singular forms "a," "an" and "the" include plural referents unless the context clearly dictates otherwise.

As used herein, "about" means approximately or nearly and in the context of a numerical value or range set forth means±15% of the numerical. Ranges disclosed herein include subsets of the specified ranges.

The term "administration", "administering", and variants thereof (e.g., "administering" a compound) is used throughout the specification to describe the delivery or introduction of the compound or a prodrug of the compound into the system of the animal in need of treatment. When a compound of the invention or prodrug thereof is provided in combination with one or more other active agents, "administration" and its variants are each understood to include concurrent and sequential introduction of the compound or prodrug thereof and other agents Compounds of the subject invention be administered a number of ways including, but not limited to, parenteral (such term referring to intravenous and intra-arterial as well as other appropriate parenteral routes), intrathecal, intraventricular, intraparenchymal (including into the spinal cord, brainstem or motor cortex), intracisternal, intracranial, intrastriatal, intranigral, inhalation, and transdermal, among others which term allows a compound of the subject invention to be carried to the ultimate target site where needed. A compound of the subject invention can be administered in the form of active compound, admixtures, or compositions thereof. The compositions according to the present invention may be used without bio-absorption enhancing agent, and/or without diluent. Alternatively, compositions according to the present invention may include one or more of the bio-absorption enhancing agent, and diluent.

Administration will often depend upon the type of cancer or precancer being targeted. For example, administration may preferably be via administration into the cerebral spinal fluid or by direct administration into the affected tissue in the brain or be via a parenteral route, for example, intravenously, for systemic/metastatic diseases.

The therapeutic compound is administered and dosed in accordance with good medical practice, taking into account the clinical condition of the individual patient, the site and method of administration, scheduling of administration, patient age, sex, body weight, and other factors known to medical practitioners.

As used herein "animal" means a multicellular, eukaryotic organism classified in the kingdom Animalia or Metazoa. The term includes, but is not limited to, mammals. Non-limiting examples include rodents, aquatic mammals, domestic animals such as dogs and cats, farm animals such as sheep, pigs, cows and horses, and humans. Wherein the terms "animal" or "mammal" or their plurals are used, it is contemplated that it also applies to any animals.

The terms "comprising," "consisting of" and "consisting essentially of" are defined according to their standard meaning. The terms may be substituted for one another throughout the instant application in order to attach the specific meaning associated with each term.

As used herein, the term "therapeutically effective amount" refers to concentrations or amounts of components of the invention that elicit the biological or medicinal response in a tissue, system, animal or human that is being sought by a researcher, veterinarian, medical doctor or other clinician. In reference to a disease, illness, condition, infection, an effective amount comprises an amount sufficient to remedy or ameliorate the disease. In some embodiments, an effective amount is an amount sufficient to delay development of disease. The therapeutically effective amount can, when used for proliferative disorder therapy, result in the amelioration of cancer or other proliferative disorders or one or more symptoms thereof, prevent advancement of cancer or other proliferative disorder, or cause regression of cancer or other proliferative disorder.

A therapeutically effective amount of the therapeutic compound refers to that amount being administered which will treat, to some extent, a cancer or precancerous formation or growth. In reference to the treatment of a cancer or precancer, a therapeutically effective amount refers to the amount which: (1) reduces the size of a tumor, (2) inhibits (i.e. stopping or slowing to some extent) tumor metastasis, (3) inhibits (i.e. stopping or slowing to some extent) tumor growth, or (4) inhibits (i.e. stopping or slowing to some extent) cellular proliferation.

As used herein, "treatment" refers to obtaining beneficial or desired clinical results. Beneficial or desired clinical results include, but are not limited to, any one or more of: alleviation of one or more symptoms, diminishment of extent of infection, stabilization (i.e., not worsening) of the state of infection, preventing or delaying spread of the disease (such as pathogen growth or replication), preventing or delaying occurrence or recurrence of the disease, delay or slowing of disease progression and amelioration of the disease state. The methods of the invention contemplate any one or more of these aspects of treatment. The term treatment, as used in this definition only, is intended to mean that regiment described is continued until the underlying disease is resolved, whereas therapy requires that the regiment alleviate one or more symptoms of the underlying disease. Prophylaxis means that regiment is undertaken to prevent a possible occurrence, such as where a pre-cancerous lesion is identified.

The term "patient" is used herein to describe members of the animal kingdom, as defined above. The patient may be any animal requiring therapy, treatment, or prophylaxis, or any animal suspected of requiring therapy, treatment, or prophylaxis.

As used herein, the term "proliferative disorders" broadly encompasses any neoplastic disease(s) including those which are potentially malignant (pre-cancerous) or malignant (cancerous) and covers the physiological condition in mammals that is typically characterized by unregulated cell growth. The term therefore encompasses the treatment of tumors. Examples of such proliferative disorders include cancers such as carcinoma, lymphoma, blastoma, sarcoma, and leukemia, as well as other cancers disclosed herein. The compositions disclosed herein are useful for treating all types of cancer, and include breast cancer; ovarian cancer, multiple myeloma tumor specimens, pancreatic cancer and blood malignancies, such as acute myelogenous leukemia, (Turkson, et al., U.S. Pat. No. 8,609,639; Jove, et al., WO 00/44774), multiple myeloma, acute myelogenous leukemia (Dalton, et al., PCT/US2000/001845), head and neck cancer, lung cancer, colorectal carcinoma, prostate cancer, melanoma, sarcoma, liver cancer, brain tumors, multiple myeloma, leukemia, cervical cancer, colorectal carcinoma, liver cancer, gastric cancer, prostate cancer, renal cell carcinoma, hepatocellular carcinomas, gastric cancers, and lymphomas (Li, et al., U.S. application Ser. No. 12/677, 513), fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, a seminoma, an embryonal carcinoma, Wilms' tumor, testicular tumor, lung carcinoma, small cell lung carcinoma, bladder carcinoma, epithelial carcinoma, a glioma, an astrocytoma, medulloblastoma, craniopharyngioma, ependymoma, pinealoma, hemangioblastoma, acoustic neuroma, oligodendroglioma, meningioma, neuroblastoma, retinoblastoma; acute lymphocytic leukemia, acute myelocytic leukemia, chronic leukemia, and polycythemia vera (Jove, et al., U.S. application Ser. No. 10/383,707).

A "safe and effective amount" refers to the quantity of a component that is sufficient to yield a desired therapeutic response without undue adverse side effects (such as toxicity, irritation, or allergic response) commensurate with a reasonable benefit/risk ratio when used in the manner of this invention.

The terms "small interfering RNA" or "siRNA" and "short hairpin RNA" or "shRNA" are used herein to refer to any nucleic acid molecule capable of mediating RNA interference (RNAi) or gene silencing. (See e.g., Bass, The short answer. Nature. 2001 May 24 411(6836):28-429; Elbashir, et al. Duplexes of 21-nucleotide RNAs mediate RNA interference in cultured mammalian cells. Nature. 2001 May 24; 411(6836): 494-498; Kreutzer & Limmer (WO 00/448953; Evans, et al. (WO 01/36646); and Li, et al. (WO 00/44914)). In some embodiments, an siRNA or shRNA is provided that comprises a double-stranded polynucleotide molecule comprising complementary sense and antisense regions, wherein the antisense region comprises a sequence complementary to a region of a target nucleic acid molecule (for example, a nucleic acid molecule encoding p53 R175H mutated protein, or other mutation in p53). In another embodiment, an siRNA or shRNA is provided that comprises a single stranded polynucleotide having self-complementary sense and antisense regions, wherein the antisense region comprises a sequence complementary to a region of a target nucleic acid molecule. In another embodiment, an siRNA or shRNA molecule can be provided that comprises a single stranded polynucleotide having one or more loop structures and a stem comprising self-complementary sense and antisense regions, wherein the antisense region comprises a sequence complementary to a region of a target nucleic acid molecule, and wherein the polynucleotide can be processed either in vivo or in vitro to generate an active siRNA or shRNA capable of mediating RNAi. As used herein, siRNA or shRNA molecules need not be limited to those molecules containing only RNA, but further encompass chemically modified nucleotides and non-nucleotides.

A "pharmaceutically acceptable" component is one that is suitable for use with humans and/or animals without undue adverse side effects (such as toxicity, irritation, and allergic response) commensurate with a reasonable benefit/risk ratio.

The pharmaceutical compositions of the subject invention can be formulated according to known methods for preparing pharmaceutically useful compositions.

As used herein, the phrase "pharmaceutically acceptable carrier" means any of the standard pharmaceutically acceptable carriers, such as a solvent, suspending agent or vehicle, for delivering the compound or compounds in question to the animal or human. The carrier may be liquid or solid and is selected with the planned manner of administration in mind. The pharmaceutically acceptable carrier can include diluents, adjuvants, and vehicles, as well as implant carriers, and inert, non-toxic solid or liquid fillers, diluents, or encapsulating material that does not react with the active ingredients of the invention. Liposomes and micelles are also a pharmaceutical carrier. Examples of carriers include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations are described in a number of sources that are well known and readily available to those skilled in the art. For example, Remington's Pharmaceutical Sciences (Martin E W [1995] Easton Pa., Mack Publishing Company, 19.sup.th ed.) describes formulations which can be used in connection with the subject invention. The carrier includes any and all solvents, dispersion media, vehicles, coatings, diluents, antibacterial and antifungal agents, isotonic and absorption delaying agents, buffers, carrier solutions, suspensions, colloids, and the like. Formulations suitable for parenteral administration include, for example, aqueous sterile injection solutions, which may contain antioxidants, buffers, bacteriostats, and solutes which render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the formulations of the subject invention can include other agents conventional in the art having regard to the type of formulation in question. The pharmaceutical composition can be adapted for various forms of administration. Administration can be continuous or at distinct intervals as can be determined by a person skilled in the art.

The compounds of the present invention include all hydrates and pharmaceutically acceptable salts of the propanoic acids that can be prepared by those of skill in the art, for example by reacting the inventive compound with a sufficiently basic compound, such as an amine, affording a physiologically acceptable anion. Under conditions where the compounds of the present invention are sufficiently basic or acidic to form stable nontoxic acid or base salts, administration of the compounds as salts may be appropriate. Suitable inorganic salts may also be formed by reaching the compound with a basic compound, such as a basic salt of ammonium, calcium magnesium, potassium, or sodium, such as ammonium bicarbonate. When reference is made to a compound or administering a compound, the recitation of the compound includes a pharmaceutically acceptable salt thereof.

The compounds of the present invention can be formulated as pharmaceutical compositions and administered to a patient, such as a human patient, in a variety of forms adapted to the chosen route of administration, e.g., orally or parenterally, by intravenous, intramuscular, topical, or subcutaneous routes.

Sterile injectable solutions are prepared by incorporating the active compound in the required amount in the appropriate solvent with several of the other ingredients enumerated above, as required, followed by filter sterilization. In the case of sterile powders for the preparation of sterile injectable solutions, the preferred methods of preparation are vacuum drying and the freeze-drying techniques, which yield a powder of the active ingredient plus any additional desired ingredient presenting the previously sterile-filtered solutions.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from adsorbent pads, used to impregnate bandages and other dressings, or sprayed onto the affected area using pump-type or aerosol sprayers.

Useful dosages of the compounds of the present invention can be determined by comparing their in vitro activity, and in vivo activity in animal models. Methods for the extrapolation of effective dosages in mice, and other animals, to humans are known to the art (See, Borch et al., U.S. Pat. No. 4,938,949).

Accordingly, the invention includes a pharmaceutical composition comprising a compound of the present invention as described above, or a pharmaceutically acceptable salt thereof, in combination with a pharmaceutically acceptable carrier.

Pharmaceutical compositions adapted for oral, topical or parenteral administration, comprising an amount of one or more compounds effective to treat a bacterial infection, are a preferred embodiment of the invention.

The process introduced herein uses copies of the wild-type p53 mRNA, for generating wild-type p53 (wt p53) proteins, and provides them to selected cells in the body.

Example 1

Wild-type p53 (wt p53) mRNA is synthesized to increase the stability of the mRNA, thereby resulting in increased lifespan of the wt p53 in the cells and increasing the amount of wt p53 protein translation and resulting wt p53 in the cell.

Wild-type p53 mRNA is purified from MCF7 cell line (Cat. No. HTB-22, American Type Culture Collection, Manassas, Va.) and subjected to reverse transcription PCR (RT-PCR). Briefly, cells are trypsinized and suspended in PBS, followed by moving the cells to an extraction tube (FastRNA Pro Green; BioRad). The cells are centrifuged, washed with 1×PBS, and the PBS removed, followed by addition of lysis buffer treated with RNase Inhibitor Protein (hPRI, ThermoFisher), and DNase. The cells are incubated on ice for 30 minutes, sonicated and placed in a centrifuge tube and centrifuged at 12,000 rpm for 10 minutes at 4° C. The RNA quality and amount are then measured by UV spectroscopy at 260 nm and 50 ug loaded into a PAGE gel possessing ethidium bromide in MOPS buffer containing 3.7% formaldehyde. The RNA is loaded at 4 V/cm for about 5 hours (until dye migrated 3 cm into the gel) followed by 6V/cm. The bands at the 53 kDa position are excised and purified from the gel.

Modified p53 ORF mRNA is synthesized using site directed mutagenesis to increase the stability of the p53 mRNA. (Wu, et al., Translation affects mRNA stability in a codon-dependent manner in human cells. Elife. 2019 Apr. 23; 8:e45396; Nagata, et al., Synthesis and biological activity of artificial mRNA prepared with novel phosphorylating reagents. Nucleic Acids Res. 2010 November; 38(21):7845-7857; Thess, et al., Sequence-engineered mRNA without chemical nucleoside modifications enables an effective protein therapy in large animals. Mol Ther. 2015 September; 23(9):1456-1464; Avci-Adali, et al., In vitro synthesis of modified mRNA for induction of protein expression in human cells. J Vis Exp. 2014 Nov. 13; (93):51943; Dvir, et al., Deciphering the rules by which 5'-UTR sequences affect protein expression in yeast. Proc Natl Acad Sci USA. 2013 Jul. 23; 110(30):e2792-2801). In site directed mutagenesis, substitutions of the wild-type p53 mRNA are performed to create the synthetic mRNA possessing increased stability. A mutated primer sequence having base pairs matching the construct sequence flanking the mutation was constructed. Alternatively, for primers containing multiple mutations, the mutations are surrounded by base pairs matching the construct, and base pairs matching the construct flanking the outermost mutations. The p53 mRNA, is annealed with the primers using polymerase chain reaction (PCR), the temperature of which is typically around 60° C., but can be altered based on homology of the primer to the construct and percentage of G-C versus A-T in the sequence. PCR extension is performed on the primer, using cDNA from the mRNA construct as a template, thereby forming a synthetic cDNA possessing the desired substitutions. The template p53 DNA is then degraded, leaving only the remaining specifically mutated DNA strand.

A 5' cap analog, which is important to translation of mRNA, can be 7mG(5')ppp(5')$N_1$pNp, which is a common 5' cap analog. (Banerjee, 5'-teminal cap structure in eucaryotic messenger ribonucleic acids. Microbiol Rev. 1980 June; 44(2):175-205). The 5' UTR has the following sequence, identified as SEQ ID No. 1:

cucaaaaguc uagagccacc guccagggag cagguagcug cugggcuccg gggacacuuu gcguucgggc ugggagcgug cuuuccacga cggugacacg cuucccugga uuggcagcca gacugccuuc cggguca-cug cc The open reading frame encoding a p53 protein is a nucleotide protein coding sequence which, when translated, generates a wild-type p53 protein, the function of which is to enable the said protein to conduct proper surveillance inside the body's cells and act to destroy cells which have become or are about to become cancerous. Wild-type p53 mRNA has the following sequence, identified as SEQ ID No. 2:

aug gag gag ccg cag uca gau ccu agc guc gag ccc ccu cug agu cag gaa aca uuu uca gac cua ugg aaa cua cuu ccu gaa aac aac guu cug ucc ccc uug ccg ucc caa gca aug gau gau uug aug cug ucc ccg gac gau auu gaa caa ugg uuc acu gaa gac cca ggu cca gau gaa gcu ccc aga aug cca gag gcu gcu ccc ccc gug gcc ccu gca cca gca gcu ccu aca ccg gcg gcc ccu gca cca gcc ccc ucc ugg ccc cug uca ucu ucu guc ccu ucc cag aaa acc uac cag ggc agc uac ggu uuc cgu cug ggc uuc uug cau ucu ggg aca gcc aag ucu gug acu ugc acg uac ucc ccu gcc cuc aac aag aug uuu ugc caa cug gcc aag acc ugc ccu gug cag cug ugg guu gau ucc aca ccc ccg ccc ggc acc cgc guc cgc gcc aug gcc auc uac aag cag uca cag cac aug acg gag guu gug agg cgc ugc ccc cac cau gag cgc ugc uca gau agc gau ggu cug gcc ccu ccu cag
cau cuu auc cga gug gaa gga aau uug cgu gug gag
uau uug gau gac aga aac acu uuu cga cau agu gug
gug gug ccc uau gag ccg ccu gag guu ggc ucu gac
ugu acc acc auc cac uac aac uac aug ugu aac agu
ucc ugc aug ggc ggc aug aac cgg agg ccc auc cuc
acc auc auc aca cug gaa gac ucc agu ggu aau cua
cug gga cgg aac agc uuu gag gug cgu guu ugu gcc
ugu ccu ggg aga gac cgg cgc aca gag gaa gag aau
cuc cgc aag aaa ggg gag ccu cac cac gag cug ccc
cca ggg agc acu aag cga gca cug ccc aac aac acc
agc ucc ucu ccc cag cca aag aag aaa cca cug gau
gga gaa uau uuc acc cuu cag auc cgu ggg cgu gag
cgc uuc gag aug uuc cga gag cug aau gag gcc uug
gaa cuc aag gau gcc cag gcu ggg aag gag cca ggg
ggg agc agg gcu cac ucc agc cac cug aag ucc aaa
aag ggu cag ucu acc ucc cgc cau aaa aaa cuc aug
uuc aag aca gaa ggg ccu gac uca gac uga

A modified first p53 mRNA (Wu, et al., Translation affects mRNA stability in a codon-dependent manner in human cells. Elife. 2019 Apr. 23; 8:e45396) has the following sequence, identified as SEQ ID No. 3:

aug gag gag ccg cag uca gau ccc agc guc gag ccc
ccc cug agu cag gag acg uuc uca gac cua ugg aaa
cua cuc ccc gag aac aac gug cug ucc ccc uug ccg
ucc caa gca aug gau gau uug aug cug ucc ccg gac
gau auu gag caa ugg uuc acg gag gac cca ggu cca
gau gag gcu ccc aga aug cca gag gcu gcu ccc ccc
gug gcc ccc gca cca gca gcu ccc acg ccg gcg gcc
ccc gca cca gcc ccc ucc ugg ccc cug uca ucu ucu
guc ccc ucc cag aaa acc uac cag ggc agc uac ggu
uuc cgg cug ggc uuc uug cau ucu ggg acg gcc aag
ucu gug acg ugc acg uac ucc ccc gcc cuc aac aag
aug uuc ugc caa cug gcc aag acc ugc ccc gug cag
cug ugg gug gau ucc acg ccc ccg ccc ggc acc cgc
guc cgc gcc aug gcc auc uac aag cag uca cag cac
aug acg gag gug gug agg cgc ugc ccc cac cau gag
cgc ugc uca gau agc gau ggu cug gcc ccc ccc cag
cau cuc auc cga gug gag gga aac uug cgg gug gag -continued uac uug gau gac aga aac acg uuc cga cau agu gug
gug gug ccc uac gag ccg ccc gag gug ggc ucu gac
ugu acc acc auc cac uac aac uac aug ugu aac agu
ucc ugc aug ggc ggc aug aac cgg agg ccc auc cuc
acc auc auc acg cug gag gac ucc agu ggu aac cua
cug gga cgg aac agc uuc gag gug cgg gug ugu gcc
ugu ccc ggg aga gac cgg cgc acg gag gag gag aac
cuc cgc aag aaa ggg gag ccc cac cac gag cug ccc
cca ggg agc acg aag cga gca cug ccc aac aac acc
agc ucc ucu ccc cag cca aag aag aaa cca cug gau
gga gag uac uuc acc cuc cag auc cgg ggg cgg gag
cgc uuc gag aug uuc cga gag cug aac gag gcc uug
gag cuc aag gau gcc cag gcu ggg aag gag cca ggg
ggg agc agg gcu cac ucc agc cac cug aag ucc aaa
aag ggu cag ucu acc ucc cgc cau aaa aaa cuc aug
uuc aag acg gag ggg ccc gac uca gac uga

A modified second p53 mRNA has the sequence, identified as SEQ ID No. 4:

aug gag gag ccg cag uca gau ccc agc guc gag ccc
ccc cug agu cag gag acc uuc uca gac cua ugg aaa
cua cug ccc gag aac aac guc cug ucc ccc uug ccg
ucc caa gca aug gau gau uug aug cug ucc ccg gac
gau auu gag caa ugg uuc acc gag gac cca ggu cca
gau gag gcu ccc aga aug cca gag gcu gcu ccc ccc
gug gcc ccc gca cca gca gcu ccc acc ccg gcg gcc
ccc gca cca gcc ccc ucc ugg ccc cug uca ucu ucu
guc ccc ucc cag aaa acc uac cag ggc agc uac ggu
uuc cgg cug ggc uuc uug cau ucu ggg acc gcc aag
ucu gug acc ugc acg uac ucc ccc gcc cuc aac aag
aug uuc ugc caa cug gcc aag acc ugc ccc gug cag
cug ugg guc gau ucc acc ccc ccg ccc ggc acc cgc
guc cgc gcc aug gcc auc uac aag cag uca cag cac
aug acg gag guc gug agg cgc ugc ccc cac cau gag
cgc ugc uca gau agc gau ggu cug gcc ccc ccc cag
cau cug auc cga gug gag gga aac uug cgg gug gag
uac uug gau gac aga aac acc uuc cga cau agu gug
gug gug ccc uac gag ccg ccc gag guc ggc ucu gac
ugu acc acc auc cac uac aac uac aug ugu aac agu
ucc ugc aug ggc ggc aug aac cgg agg ccc auc cuc
acc auc auc acc cug gag gac ucc agu ggu aac cua

```
cug gga cgg aac agc uuc gag gug cgg guc ugu gcc ugu ccc ggg aga gac cgg cgc acc gag gag gag aac cuc cgc aag aaa ggg gag ccc cac cac gag cug ccc cca ggg agc acc aag cga gca cug ccc aac aac acc agc ucc ucu ccc cag cca aag aag aaa cca cug gau gga gag uac uuc acc cug cag auc cgg ggg cgg gag cgc uuc gag aug uuc cga gag cug aac gag gcc uug gag cuc aag gau gcc cag gcu ggg aag gag cca ggg ggg agc agg gcu cac ucc agc cac cug aag ucc aaa aag ggu cag ucu acc ucc cgc cau aaa aaa cuc aug uuc aag acc gag ggg ccc gac uca gac uga
```

The 3' UTR has the following sequence, identified as SEQ ID No. 5:

```
cauucu ccacuucuug uuccccacug acagccuccc acccccaucu cucccucccc ugccauuuug gguuuugggu cuuugaaccc uugcuugcaa uaggugugcg ucagaagcac ccaggacuuc cauuugcuuu gucccggggc uccacugaac aaguuggccu gcacuggugu uuuguugugg ggaggaggau gggagguagg acauaccagc uuagauuuua agguuuuuac ugugagggau guuugggaga uguaagaaau guucuugcag uuaaggguua guuuacaauc agccacauuc uagguagggg cccacuucac cguacuaacc agggaagcug ucccucacug uugaauuuuc ucuaacuuca aggcccauau cugugaaaug cuggcauuug caccuaccuc acagagugca uugugagggu uaaugaaaua auguacaucu ggccuugaaa ccaccuuuua uuacaugggg ucuagaacuu gaccccuug agggugcuug uucccucucc cuguuggucg gugggguugu aguuucuaca guuggggcagc ugguuaggua gagggaguug ucaagucucu gcuggcccag ccaaacccug ucugacaacc ucuuggugaa ccuuaguacc uaaaaggaaa ucucacccca ucccacaccc uggaggauuu caucucuugu auaugaugau cuggauccac caagacuugu uuuaugcuca ggucaauuu cuuuuucuu uuuuuuuuu uuuuucuuu uucuuugaga cugggucucg cuuuguugcc caggcuggag uggaguggcg ugaucuuggc uuacugcagc cuuugccucc ccggcucgag caguccugcc ucagccuccg gaguagcugg gaccacaggu ucaugccacc auggccagcc aacuuuugca uguuuguag agauggggggc ucacaguguu gccaggcug gucucaaacu ccugggcuca ggcgauccac cugucucagc cucccagagu gcugggauua caauugugag ccaccacguc cagcuggaag ggucaacauc uuuuacauuc ugcaagcaca ucugcauuuu cacccaccc uuccccuccu ucucccuuuu uauaucccau uuuuauaucg aucucuuauu uuacaauaaa acuuugcugc ca
```

The poly adenine tail (poly(A) tail) is a region of mRNA that is directly downstream from the 3' UTR. The poly(A) tail contains one or more consecutive adenine nucleotides. The poly(A) tail of an mRNA is generally utilized by the ribosome translation complexes to determine how many times the mRNA is to be translated. Generally with each translation, one adenosine monophosphate is removed from the poly(A) tail. Once all of the adenosine monophosphates have been removed from an mRNA's poly(A) tail, the mRNA is enzymatically degraded The sequence-engineered optimized open reading frame (ORF) mRNAs, seen in SEQ ID. Nos 2-4, are appended with a cap, a 5'-UTR from HSD17B4 (hydroxysteroid (17-β) dehydrogenase 4), a 3'-UTR from ALB (albumin), and a poly(A) tail. For capping of the RNA, m7G capping and 2'-O-methyltransferase kits (CellScript, Madison, Wis.) are used. The p53 gene is reverse transcribed from the mRNA and the cDNA is inserted into a circular plasmid harboring the sequence of interest downstream of a T7 promoter and ampicillin resistance. The plasmid was inserted into E. coli using previous methods. (Avci-Adali, et al., In vitro synthesis of modified mRNA for induction of protein expression in human cells. J Vis Exp. 2014 Nov. 13; (93):51943). Briefly, cells are grown in Soc medium and heat shocked with around 10 pg to 100 ng of plasmid to introduce the plasmid into the bacteria. The E. coli is then grown on agar plates possessing 100 μg/ml ampicillin. The colonies of cells are collected, and p53 cDNA is harvested from the cells as described previously.

The p53 cDNA is amplified using PCR, as described previously, (Lorenz, Polymerase chain reaction: basic protocol plus troubleshooting and optimization strategies. J Vis Exp. 2012; 63:3998) and transcribed to mRNA while concurrently adding a polyA tail. (Avci-Adali, et al., In vitro synthesis of modified mRNA for induction of protein expression in human cells. J Vis Exp. 2014 Nov. 13; (93): 51943). Briefly, the amplified cDNA is mixed with NTP and T7 RNA polymerase (Thermo Scientific, Braunschweig, Germany) or T3 polymerase or Sp6 phage RNA polymerase, and a poly T-tail of 120 thymidines (T) is added to the insert by using a reverse primer with a $T_{120}$ extension forming mRNAs obtain a poly A-tail with a defined length after the IVT. (Avci-Adali, et al., In vitro synthesis of modified mRNA for induction of protein expression in human cells. J Vis Exp. 2014 Nov. 13; (93):51943; Pardi, et al., In vitro transcription of long RNA containing modified nucleosides. Methods Mol Biol. 2013; 969:29-42). The DNA is removed using DNase (2 U) and incubated for 15 minutes at 37° C., and treated with 2U of Antarctic phosphatase and is incubated at 37° C. for 30 min to remove 5' triphosphates to reduce the immunicity of the mRNA due to RIG-I. The RNA is purified using an RNA purification kit, and the purity and concentration of RNA determined using optical density $A_{260}/A_{280}$ and $A_{260}/A_{230}$. The RNA is loaded into the carrier, described in the Examples below.

Other methods can be used to generate synthesized p53 mRNA having the sequences listed above. (See, Nagata, et al., Synthesis and biological activity of artificial mRNA prepared with novel phosphorylating reagents. Nucleic Acids Res. 2010 November; 38(21):7845-7857).

Example 2

Engineered RNAi molecules, introduced into host cells or whole organisms (subjects) as described herein, will lead to an siRNA molecule, ds RNA, miRNA or other RNAi molecule associating with endogenous protein components of the RNAi pathway to bind to and target a specific mutated p53 mRNA sequence for cleavage and destruction. In this fashion, the mutated p53 mRNA can be targeted by the RNAi to deplete the mutated p53 from a cell, leading to a decrease in the concentration of the mutated p53 protein encoded by that mRNA in the cell or organism.

RNA interference (RNAi) is an efficient process to induce sequence-specific degradation of targeted mRNA in animal and plant cells. (Hutvagner & Zamore, RNAi: nature abhors a double-strand. Curr Opin Genet Dev. 2002 Apr. 1; 12(2): 225-232; Sharp, RNA interference-2001. Genes Dev. 2001 Mar. 1; 15(5): 485-490). Double-stranded RNA (dsRNA), also referred to herein as small interfering RNA (siRNAs) or double-stranded small interfering RNAs (ds siRNA) against mutated p53 are designed to form 21-nucleotide (nt) duplexes of siRNA, or certain microRNAs (miRNA), have the capacity to trigger degradation of the target mRNA. (Chiu, et al., RNAi in human cells. Mol Cell. 2002 Sep. 1; 10(3):549-561; Elbashir, et al., Duplexes of 21-nucleotide RNAs mediate RNA interference in cultured mammalian cells. Nature. 2001 May 24; 411(6836): 494-498). After introduction into a cell, dsRNAs are cleaved by Dicer, an endoribonuclease, thereby forming around 21-23 nucleotide (nt) dsRNA having a 2-nucleotide overhang at the 3' end. (Bernstein, et al., Role for a bidentate ribonuclease in the initiation step of RNA interference. Nature. 2001 Jan. 18; 409(6818):363-366; Hammond, et al., An RNA-directed nuclease mediates post-transcriptional gene silencing in *Drosophila* cells. Nature. 2000 Mar. 16; 404(6775):293-296; Hammond, et al., Argonaute2, a link between genetic and biochemical analyses of RNAi. Science. 2001 Aug. 10; 293(5532):1146-1150; Ketting, et al., Dicer functions in RNA interference and in synthesis of small developmental timing in *C. elegans*. Genes Dev. 2001 Oct. 15; 15(20): 2654-2659). The siRNAs formed from DICER react directly with PIWI endonuclease or are incorporated into the RNA-induced silencing complex (RISC) are a primer molecule to target homologous mRNA for degradation. (Hammond, et al., An RNA-directed nuclease mediates post-transcriptional gene silencing in *Drosophila* cells. Nature. 2000; 404:293-296; Hammond, et al., Argonaute2, a link between genetic and biochemical analyses of RNAi. Science. 2001; 293: 1146-1150; Elbashir, et al., RNA interference is mediated by 21 and 22 nt RNAs. Genes Dev. 2001 Jan. 15; 15(2):188-200; Zamore, et al., RNAi: double stranded RNA directs the ATP-dependent cleavage of mRNA at 21 to 23 nucleotide intervals. Cell. 2000 Mar. 31; 101(1):25-33). The targeting occurs in a sequence-specific manner, requiring substantial similarity with the target mRNA. (Elbashir, et al., Duplexes of 21-nucleotide RNAs mediate RNA interference in cultured mammalian cells. Nature. 2001 May 24; 411(6836): 494-498; Sabariegos, et al., Sequence homology required by human immunodeficiency virus type 1 to escape from short interfering RNAs. J Virol. 2006 January; 80(2):571-577; Ui-Tei, et al., Guidelines for the selection of highly effective siRNA sequences for mammalian and chick RNA interference. Nucleic Acids Res. 2004; 32(3):936-948).

Studies have shown full RNAi requires complete homology, though partial interference can occur with substitutions at the 3' or 5' end of the siRNA. (Sabariegos, et al., Sequence homology required by human immunodeficiency virus type 1 to escape from short interfering RNAs. J Virol. 2006 January; 80(2):571-577; Ui-Tei, et al., Guidelines for the selection of highly effective siRNA sequences for mammalian and chick RNA interference. Nucleic Acids Res. 2004; 32(3):936-948). A mismatch of only 1 nucleotide can significantly decrease siRNA efficacy. (Sabariegos, et al., Sequence homology required by human immunodeficiency virus type 1 to escape from short interfering RNAs. J Virol. 2006 January; 80(2):571-577; Du, et al., A systematic analysis of the silencing effects of an active siRNA at all single-nucleotide mismatched target sites. Nucleic Acids Res. 2005; 33:1671-1677). Synthetic siRNAs are delivered into cells as described herein, resulting in short-term persistence of the silencing effect. typically around 4 to 5 days in cultured cells. (Raemdonck, et al, Maintaining the silence: reflections on long-term RNAi. Drug Discov Today. 2008 November; 13(21):917-931).

The RNAi molecules can be nucleic acid molecules that individually encode either one strand of a dsRNA or encode the entire nucleotide sequence of an RNA hairpin loop structure (siRNA or shRNA). The nucleic acid molecules or constructs of the invention include dsRNA molecules comprising 16-23 nucleotides, in each strand, wherein one of the strands is substantially identical, e.g., at least 98% (or more), to a target region in the mRNA of the subject or host cell's mutated p53 mRNA, and the other strand is identical or substantially identical to the first strand. The dsRNA molecules of the invention can be chemically synthesized, or can be transcribed in vitro from a DNA template and introduced into a cell. The dsRNA molecules can be designed using any method known in the art. Furthermore, because RNAi is believed to progress via at least one single-stranded RNA intermediate, the skilled artisan will appreciate that ss-siRNAs (e.g., the antisense strand of a ds-siRNA) can also be designed as described herein. However, the sequence should have either a A/U at the 5' end of the antisense strand; a G/C at the 5' end of the sense strand; at least five A/U residues in the 5' terminal one-third of the antisense strand; and should not include 9 nucleotides (or more) lacking either G or C. (Ui-Tei, et al., Guidelines for the selection of highly effective siRNA sequences for mammalian and chick RNA interference. Nucleic Acids Res. 2004; 32(3):936-948).

A biopsy of a tumor can be obtained to sequence the TP53 and identify mutations in the gene for RNAi targeting. The RNAi molecules are then prepared using the following methodology.

The mutated TP53 gene, or mRNA, is searched to identify AA dinucleotide sequences in the mRNA open reading frame. The subsequent, 3' adjacent 21-23 nucleotides are analyzed for G/C content; lower G/C content, i.e. from 35-55%, may be more active than those with G/C content higher than 55%. The mutated TP53 or mutated mRNA is compared to wild-type TP53 or wt p53 mRNA for sequence differences. While it is preferred to have over 5% difference between the target sequence and non-target gene products, the wild-type p53 will likely have high homology to the mutated p53, as many mutations include 1 amino acid substitution or a limited number of substitutions. However, as wt p53 mRNA is added to the cells, and RNAi is inefficient when target sequences occurring centrally in the siRNA differ, sequences differing by 1 nucleotide at the mutated p53/TP53 target versus wt p53/TP53 are acceptable. The proteosome and genome are analyzed to confirm RNAi will not interfere with other proteins in the cell that are not desired. Such analysis may occur using methods known in the art, such as performing a sequence homology search (BLAST search), which is available at the National Center for Biotechnology Information web site of the National Institutes of Health. A 3' overhang is added to the sequence to accommodate a hairpin. The dsRNA is synthesized having a hairpin of about 19-29 base pairs with complementary sides to form the loop, and complementary strands of RNA for form dsRNA using solid-phase synthesis or other methods known in the art. (Gaglione, et al., Synthesis and gene silencing properties of siRNAs containing terminal amide linkages. Biomed Res Int. 2014 Mar. 26; 2014:901617; Dong, et al., Strategies, design, and chemistry in siRNA delivery systems. Adv Drug Deliv Rev. 2019 April; 144: 133-147; Zamecnik & Stephenson, Inhibition of Rous-sarcoma virus-replication and cell transformation by a specific oligodeoxynucleotide. Proc Nat Acad Sci USA. 1978 January; 75(1):280-284; Stephenson & Zamecnik, Inhibition of Rous sarcoma viral RNA translation by a specific oligodeoxynucleotide. Proc Nat Acad Sci USA. 1978 January; 75(1):285-288).

The nucleic acid compositions of the invention are incorporated into a carrier, such as incorporation into a nanoparticle, or can be conjugated to another moiety, such as a PEG or PEI carrier. The RNAi molecules can be functionalized for conjugation to other carriers, such as by diamide oxidation reaction or addition to functionalized hydroxyl moieties using phosphorylation reactions. (Gaglione, et al., Synthesis and gene silencing properties of siRNAs containing terminal amide linkages. Biomed Res Int. 2014 Mar. 26; 2014: 901617; Dong, et al., Strategies, design, and chemistry in siRNA delivery systems. Adv Drug Deliv Rev. 2019 April; 144: 133-147; Dong, et al., Strategies, design, and chemistry in siRNA delivery systems. Adv Drug Deliv Rev. 2019 April; 144: 133-147). Other methods known in the art can similarly be used. (Schwab et al., An approach for new anticancer drugs: oncogene-targeted antisense DNA. Ann. Oncol. 1994; 5 Suppl 4: 55-8; Godard, et al., Antisense effects of cholesterol-oligodeoxynucleotide conjugates associated with poly(alkylcyanoacrylate) nanoparticles. Eur. J. Biochem. 1995 Sep. 1; 232(2): 404-10).

Approximately 30% of the cancers having mutated p53 possess a mutation at one of six locations in the polypeptide; residue 175, 245, 248, 249, 273, or 282, as shown in Table 1. (Baugh, et al., Why are there hotspot mutations in the TP53 gene in human cancers? Cell Death Diff. 2018 January; 25(1):154-160). Accordingly, the RNAi can be developed using the most-common p53 mutations and most deleterious p53 mutations. In such examples, the dsRNA is synthesized as discussed above, using preselected p53 sequences provided below. The RNAi molecules can be directed to only 1 mutation listed, or multiple mutations listed.

TABLE 1

Common p53 mutations and minimally-functioning proteins found in human cancers. Higher VIPUR scores indicate lower functionality in the protein.

| Amino acid mutation | Frequency (%) | VIPUR score | Mutated codon |
| --- | --- | --- | --- |
| R175H | 5.6 | 0.742 | CGC→ CAC |
| G245S | 2.11 | 0.407 | GGC→ AGC |
| R248Q | 4.37 | 0.135 | CGG→ CAG |
| R248W | 3.53 | 0.185 | CGG→ UGG |
| R249S | 2.04 | 0.302 | AGG→ AGC |

TABLE 1-continued

Common p53 mutations and minimally-functioning proteins found in human cancers. Higher VIPUR scores indicate lower functionality in the protein.

| Amino acid mutation | Frequency (%) | VIPUR score | Mutated codon |
| --- | --- | --- | --- |
| R273H | 3.95 | 0.655 | CGU→ CAU |
| R273C | 3.31 | 0.947 | CGU→ UGU |
| R282W | 2.83 | 0.656 | CGG→ UGG |
| C176F | 0.95 | 0.982 | UGC→ UUC |
| R280T | 0.5 | 0.907 | AGA→ ACA |
| C141Y | 0.47 | 0.953 | UGC→ UAU |
| C176Y | 0.47 | 0.979 | UGC→ UAC |
| C135Y | 0.43 | 0.962 | UGC→ UAC |
| C238Y | 0.42 | 0.953 | UGU→ UAU |
| P278L | 0.4 | 0.952 | CCU→ CUU |
| C275Y | 0.39 | 0.99 | UGU→ UAU |
| G266R | 0.36 | 0.995 | GGA→CGA |

The following identifies target sequences for RNA interference. As is known in the art, the sequence can vary by inclusion of additional nucleotides or removal of nucleotides, provided the full sequence contains the necessary 16-23 nucleotides, in each strand. Preferably, the mutation will remain centralized in the strand, providing specificity to the RNAi molecule.

The target sequence for siRNA for p53$^{R175H}$ has the following sequence, identified as SEQ ID No. 6, which can be used for synthetic siRNA:

guu gug agg cac ugc ccc cac

The target sequence for siRNA for p53$^{G245S}$ has the following sequence, identified as SEQ ID No. 7:

ucc ugc aug agc ggc aug aac

The target sequence for siRNA for p53$^{R248Q}$ has the following sequence, identified as SEQ ID No. 8:

ggc aug aac cag agg ccc auc

The target sequence for siRNA for p53$^{R248W}$ has the following sequence, identified as SEQ ID No. 9:

ggc aug aac ugg agg ccc auc

The target sequence for siRNA for p53$^{R249S}$ has the following sequence, identified as SEQ ID No. 10:

aug aac cgg agc ccc auc cuc

The target sequence for siRNA for p53$^{R273H}$ has the following sequence, identified as SEQ ID No. 11:

uuu gag gug cau guu ugu gcc

The target sequence for siRNA for p53$^{R273C}$ has the following sequence, identified as SEQ ID No. 12:

uuu gag gug ugu guu ugu gcc

The target sequence for siRNA for p53$^{R282W}$ has the following sequence, identified as SEQ ID No. 13:

ggg aga gac ugg cgc aca gag

The target sequence for siRNA for p53$^{C176F}$ has the following sequence, identified as SEQ ID No. 14:

gug agg cgc uac ccc cac cau

The target sequence for siRNA for p53$^{C135Y}$ has the following sequence, identified as SEQ ID No. 15:

aag aug uuu uac caa cug gcc

The target sequence for siRNA for p53$^{C238Y}$ has the following sequence, identified as SEQ ID No. 16:

aac uac aug uau aac agu ucc

The target sequence for siRNA for p53$^{P278L}$ has the following sequence, identified as SEQ ID No. 17:

ugu gcc ugu cuu ggg aga gac

The target sequence for siRNA for p53$^{C275Y}$ has the following sequence, identified as SEQ ID No. 18:

gug cgu guu uau gcc ugu ccu

The target sequence for siRNA for p53$^{G266R}$ has the following sequence, identified as SEQ ID No. 19:

aau cua cug cga cgg aac agc

Example 3

Niosomes have shown benefits over liposomes in that the synthetic niosomes appear more chemically stable as vesicles, are easier to transport and store, are less expensive to manufacture, and possess increased permeability to the blood brain barrier. It is composed of synthetic amphiphilic surfactants and cholesterol that make up a bilayer membrane that is able to entrap hydrophilic solutions in the aqueous core of the vesicle.

Figure 1B:
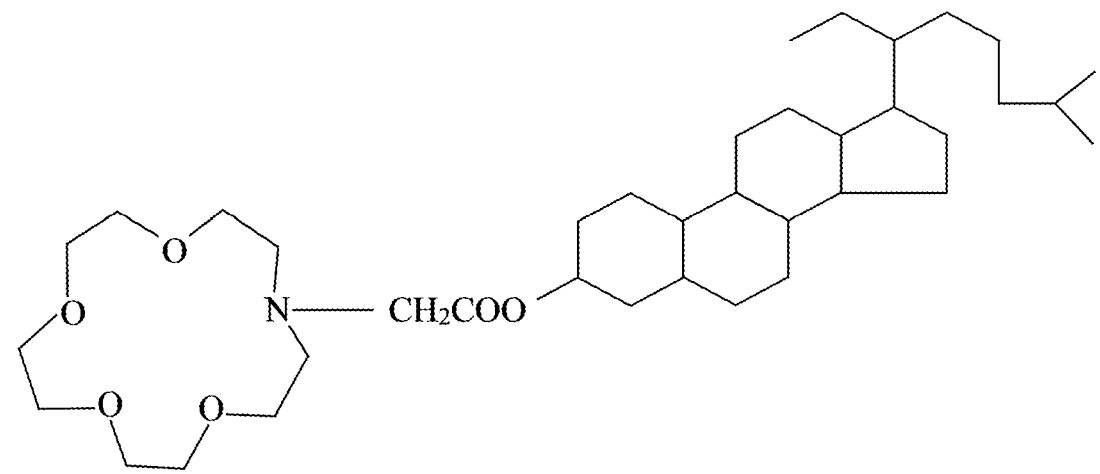
FIG. 1(b) is a structural formula of an exemplary crown ether for an embodiment of the carrier.

Exemplary surfactants include, without limiting the scope of the invention, crown ether amphiphiles bearing a steroidal moiety, 1,2-dialkyl glycerol polyoxyethylene ether, hexadecyl poly-5-oxyethylene ether, hexadecyl poly-5-oxyethylene ether ($C_{16}EO_5$); octadecyl poly-5-oxyethylene ether ($C_{18}EO_5$); hexadecyl diglycerol ether ($C_{16}G2$); sorbitan monopalmitate (Span 40) and sorbitan monostearate (Span 60), Solulan™ C24 (poly-24-oxyethylene cholesteryl ether), polysorbate 20, Span detergents, Brij detergents, such as Brij-35, and polyoxyethylene. Examples of crown ethers are illustrated in FIGS. 1(a) and 1(b), and are known in the art (Montserrat, et al., Light-induced charge injection in functional crown ether vesicles. J Am Chem Soc. 1980 Aug. 1; 102(17):5527-5529; Darwish & Uchegbu, The evaluation of crown ether based niosomes as cation containing and cation sensitive drug delivery systems. Int J Pharm. 1997 Dec. 15; 159(2):207-213; Uchegbu & Duncan, Niosomes containing N-(2-hydroxypropyl)methacrylamide copolymer-doxorubicin (PK1): effect of method of preparation and choice of surfactant on niosome characteristics and a preliminary study of body distribution. Int J Pharm. 1997 Sep. 12; 155(1):7-17). Exemplary solvents involved in noisome formation may include glycerol, oil, water, and combinations thereof.

Cholesterol stabilizes the vesicles by decreasing the permeability and enhancing solute retention (Uchegbu & Florence, Non-ionic surfactant vesicles (niosomes): physical and pharmaceutical chemistry. Adv Colloid Interface Sci. 1995 Jun. 27; 58(1):1-55; Nasseri, Effect of cholesterol and temperature in the elastic properties of niosomal membranes. Int J Pharm. 2005 Aug. 26; 300(1-2):95-101). In addition, negative charged molecules may be added to the bilayer-producing compounds, such as dicetyl phosphate, cetyl sulphate, phosphatidic acid, phosphatidyl serine, oleic acid, palmitic acid, which provide electrostatic stabilization to the vesicles and prevents vesicle aggregation (Uchegbu & Vyas, Non-ionic Surfactant Based Vesicles (Niosomes) in Drug Delivery. Int J Pharm., 1998 Oct. 15; 172(1-2):33-70; Manosroi, et al., Characterization of vesicles prepared with various non-ionic surfactants mixed with cholesterol. Colloids Surf B. 2003 Jul. 1; 30(1-2):129-138). The ability of the surfactant to form a vesicle depends on two factors, the Hydrophobic Lipophilic Balance (HLB) and the Critical Packing Parameter (CPP). The HLB is calculated using $$HLB = 20 \times Mh/M \quad (1)$$

where Mh is the molecular mass of the hydrophilic portion of the surfactant, and M is the molecular mass of the whole niosome, giving a result on an arbitrary scale of 0 to 20. For the surfactant sorbitan monostearate, an HLB number between 4 and 8 was found to be compatible with vesicle formation (Uchegbu & Vyas, Non-ionic Surfactant Based Vesicles (Niosomes) in Drug Delivery. Int J Pharm., 1998 Oct. 15; 172(1-2):33-70).

The CPP is a dimensionless number that predicts the ability of the amphiphile to form aggregates, with values of 0.5-1.0 predicting that the amphiphile will form a vesicle. (Israelachvili, Intermolecular and Surface Forces: With Applications to Colloidal and Biological Systems. 3d Ed. 2011, Orlando: Academic Press). CPP is calculated using $$CPP = v/l_c a_o \quad (2)$$

where v=hydrocarbon chain volume, $l_c$=critical hydrophobic chain length (the length above which the chain fluidity of the hydrocarbon may no longer exist), and $a_o$=area of hydrophilic head (Uchegbu & Florence, Non-ionic surfactant vesicles (niosomes): physical and pharmaceutical chemistry. Adv Colloid Interface Sci. 1995 Jun. 27; 58(1):1-55).

The niosomes are formed from the self-assembly of non-ionic amphiphiles in aqueous media resulting in closed bilayer structures (Uchegbu & Vyas, Non-ionic surfactant based vesicles (niosomes) in drug delivery. Int J Pharm., 1998 Oct. 15; 172(1-2):33-70). The assembly into bilayers is rarely spontaneous and usually involves some input of energy such as physical agitation or heat. Span 60, a surfactant, a cholesterol, and, optionally, dicetyl phosphate and/or sorbitan monosterate, a negatively charged molecule, are added to a flask in an organic solvent at a ratio of 1:1:(0.1), surfactant to cholesterol to dicetyl phosphate. The solution is mixed by agitation over a 60° C. bath until the solids dissolve and the solution transferred to an evaporator, such as a buchï rotary evaporator with nitrogen gas until a film forms on the flask. The flask is allowed to further dry for at least 12 hours, and the film hydrated using the mRNA solution of Example 1 or a combination of the mRNA of Example 1 and one or more interfering RNAs described in Example 2. The solution is further dried in the rotary evaporator until the thin film dissolves and the niosomes extruded at 60° C., resulting in size-limited niosomes containing mRNA. The niosomes are separated from unincorporated mRNA by centrifugation at 60000 rpm for 40 minutes.

These niosomes have been found to exhibit a linear behavior in their size distribution as the concentration of the hydrophilic component increases from 5 millimolar to 15 millimolar. (Alcantar, et al., U.S. Pat. No. 9,522,114).

Example 4

Molecules can be loaded onto the niosomes to permit the niosome delivery system to target cancer cells. Examples of methods to incorporate target molecules into the vesicle membrane are known in the art, but can include by way of non-limiting example, alpha fetoprotein, anti-bladder tumor antigen, anti-BRCA1, anti-BRCA2, beta 2 microglobulin HRP, mucin 16 (CA-125), CD10, CD107a, CD13, CD 15, CD 19, CD 20, CD 22, CD 25, CD 117, CD138, CD146, CD147, CD227, CD318, CD326, CD66, CD56, carcinoembryonic antigen, chlorotoxin (CTX), epithelial tumor antigen, melanoma-associated antigen (MAGE), cancer/testis antigen 1B (CTAG1B), transferrin, somatostatin receptor ligand, or combinations of the aforementioned molecules. (Mayo Clinic, CA 125 test. 1998-2021 Mayo Foundation for Medical Education and Research (MFMER); Luanpitpong, et al., Selective cytotoxicity of single and dual anti-CD19 and anti-CD138 chimeric antigen receptor-natural killer cells against hematologic malignancies. J Immunol Res, 2021 Jul. 11; 2021: e5562630; Restifo, et al., Adoptive immunotherapy for cancer: harnessing the T cell response. Nat Rev Immunol. 2012 Mar. 22: 12(4):269-281; Hareuveni, et al., Vaccination against tumor cells expressing breast cancer epithelial tumnor antigen. Proc Nat Acad Sci USA. 1990 December; 87(23):9498-9502; Vigneron, Human tumor antigens and cancer immunotherapy. Biomed Res int. 2015: 2015:948501; Novellino, et al., A listing of human tumor antigens recognized by T cells: March 2004 update. Cancer Immunol Immunother. 2005 March; 54(3):187-207; Mishra, et al., Role of B cell development marker CD10 in cancer progression and prognosis. Mol Biol Int. 2016; 2016:4328697; Kitahara, et al., Identification and characterization of CD107a as a marker of low reactive oxygen species in chemoresistant cells in colorectal cancer. Ann Surg Oncol. 2017 April; 24(4):1110-1119; Wang, et al., CD146, from a melanoma cell adhesion molecule to a signaling receptor. Signal Transduct Target Ther. 2020 Aug. 11; 5(1):148).

Niosomes are prepared, as described in Example 3, using PEG molecules that are modified to introduce an amino group. (Hong, et al., Efficient tumor targeting of hydroxycamptothecin loaded PEGylated niosomes modified with transferrin. J Control Release. 2009 Jan. 19; 133(2):96-102). Target molecules are conjugated to the PEG-amino group using an oxidation reaction, by oxidizing the target molecule and introducing the oxidized target molecule to the amino-PEG-niosomes. (Hong, et al., Efficient tumor targeting of hydroxycamptothecin loaded PEGylated niosomes modified with transferrin. J Control Release. 2009 Jan. 19; 133(2): 96-102).

Example 5

Lipid nanoparticles have been shown as an effective transport vehicle to deliver the mRNA to biologic target cells. (Maier et al., Biodegradable lipids enabling rapidly eliminated lipid nanoparticles for systemic delivery of RNAi therapeutics. Mol Ther. 2013 August; 21(8):1570-1578; Jayarama et al., Maximizing the potency of siRNA lipid nanoparticles for hepatic gene silencing in vivo, Angew Chem Int Ed Engl. 2012 Aug. 20, 51(34): 8529-8533; Semple et al., Rational design of cationic lipids. Nat Biotechnol. 2010 February, 28(2): 172-176). Such lipid nanoparticles are made by mixing a cationic lipid, non-cationic lipid, a polyethyleneglycol (PEG) conjugated lipid, and a structural lipid in a method similar to Example 3. In some variations, the lipid nanoparticles can be synthesized using a mixture of ionizable cationic lipid/phosphatidylcholine/cholesterol/PEG-lipid at a ratio of 50:10:38.5:1.5 mol/mol (cationic lipid: phosphatidylcholine: cholesterol: PEG-lipid), and encapsulate the mRNA at a RNA-to-total lipid ratio of ~0.05 (wt/wt). (Maier et al., Biodegradable lipids enabling rapidly eliminated lipid nanoparticles for systemic delivery of RNAi therapeutics. Mol Ther. 2013 August; 21(8):1570-1578; Jayarama et al., Maximizing the potency of SiRNA lipid nanoparticles for hepatic gene silencing in vivo, Angew Chem Int Ed Engl. 2012 Aug. 20, 51(34): 8529-8533). The interaction between the liposomes and the cargo usually relies on hydrophobic interactions or charge attractions, particularly in the case of cationic lipid delivery systems (Zelphati, et al., Intracellular delivery of proteins with a new lipid-mediated delivery system. J Biol Chem. 2001 Sep. 14, 276(37):35103-35110). Modifications to the liposomes, by adding ionizable amino lipids as cationic lipid moieties, such as 2,2-dilinoleyl-4-dimethylaminoethyl-[1,3]-dioxolane, increase stability of RNA-liposome carriers. (Jayarama et al., Maximizing the potency of siRNA lipid nanoparticles for hepatic gene silencing in vivo. Angew Chem Int Ed Engl. 2012 Aug. 20, 51(34): 8529-8533). As with niosomes, functionalization of the PEG molecules and conjugation with cancer targeting molecules can be performed, as outlined in Example 4.

Example 6

To introduce the therapeutic wild-type mRNA, coded to produce a wild-type p53 polypeptide, into a cell, may be accomplished by packing the mRNA in a polyethylene glycol (PEG)-polyamino acid block copolymer-based polyplex nanomicelle.

PEG block copolymers are formed through aminolysis of PEG-poly(β-benzyl L-aspartate) to form cationic branches. (Osada, et al., Polymeric micelles from poly(ethylene glycol)-poly(amino acid) block copolymer for drug and gene delivery. J R Soc Interface. 2009 Jun. 6; 6(Suppl 3): S325-S339; Nakanishi, et al., Study of the quantitative aminolysis reaction of poly(β-benzyl L-aspartate) (PBLA) as a platform polymer for functionality materials. React Funct Polym. 2007; 67:1361-1372; Kanayama, et al., A PEG-based biocompatible block catiomer with high buffering capacity for the construction of polyplex micelles showing efficient gene transfer toward primary cells. ChemMedChem. 2006 April; 1(4):439-444; Han, et al., Transfection study using multicellular tumor spheroids for screening non-viral polymeric gene vectors with low cytotoxicity and high transfection efficiencies. J Control Release. 2007 Aug. 16; 121(1-2):38-48). Alternatively, PEG-poly-amino acid polymers, such as PEG-poly(benzyl-L-glutamate and PEG-poly(L-lysine), are formed by nucleophilic attack of ring-opened ethylene oxide with N-carboxyanhydrides amino acids in 1,1,3,3-tetramethylguanidine. (Miyazaki, et al., One-pot synthesis of PEG-poly(amino acid) block copolymers assembling polymeric micelles with PEG-detachable functionality. ACS Biomater Sci Eng. 2019 Nov. 11; 5(11):5727-5733). The block polymers are suspended in aqueous solution containing mRNA and optionally RNA interfering molecules (siRNA or shRNA) and spontaneously form micelles having a hydrophobic core and hydrophilic shell (Kataoka, et al., Block-copolymer micelles as vehicles for drug delivery. J Control Release. 1993 May 1; 24:119-132; Akagi, et al., Biocompatible micellar nanovectors achieve efficient gene transfer to vascular lesions without cytotoxicity and thrombus formation. Gene Ther. 2007 July; 14(13):1029-1038).

Example 7 mRNA-PEI complexes can be made using commercially available linear polyethyleneimine (PEI) compounds, which have the ability to complex with RNA. The theoretical charge ratios of the mRNA, PEI, and γ-polyglutamic acid were determined using the number of phosphate groups on the mRNA, the number of nitrogen groups on PEI, and number of carboxylate groups on γ-PGA. A mRNA solution (1 mg/mL) is prepared in 1 mM sodium citrate buffer, and mixed with a PEI solution of 1 mg/mL in 5% glucose and a γ-polyglutamic acid solution in 5% glucose at a charge ratio of between 1:8:4: (mRNA/PEI/γ-PGA) to 1:8:12: (mRNA/PEI/γ-PGA). Notably the charge ratio of mRNA:PEI can vary from 1:6 to 1:14 while charge ratios of mRNA to γ-PGA can vary from 1:4 to 1:12. Studies have shown no significant toxicity at these levels. (Hamada, et al., Anionic complex with efficient expression and good safety profile for mRNA delivery. Pharmaceutics. 2021 Jan. 19; 13(1):126). Optionally, the mRNA is replaced by a mixture of p53 mRNA and RNA interfering molecules (siRNA or shRNA, referred to as RNAi), such as at a ratio of 1:0.5 (m/m, mRNA to RNAi). The solution is incubated on ice for 30 min and the mRNA-PEI complexes precipitated. Tests have shown complexed mRNA, as described above, is protected from RNase, is taken up by cells in vivo, and shows almost no immunogenicity. (Hamada, et al., Anionic complex with efficient expression and good safety profile for mRNA delivery. Pharmaceutics. 2021 Jan. 19; 13(1):126).

Example 8

Dry powder formulations of PEGylated synthetic KL4 peptide have been found effective in introducing nucleic acids into cells. $PEG_{12}KL4$ (EZBiolab, Carmel, N.J.) is mixed with p53 mRNA, discussed previously, at a ratio of 0.5:1 (w/w; PEG-KL4: mRNA) to 10:1 (w/w; PEG-KL4: mRNA) and incubated for 30 min at room temperature for form the mRNA complex. (Qiu, et al., PEGylated KL4 peptide as an effective vector for mRNA delivery on lung epithelial cells. J Control Release. 2019 Nov. 28; 314:102-115). In some variations, the mRNA and PEG-KL4 are mixed at a ratio of 2:1 to 2.5:1 (w/w mRNA to PEG-KL4). Optionally, the mRNA is replaced by a mixture of p53 mRNA and RNA interfering molecules (siRNA or shRNA, referred to as RNAi), such as at a ratio of 1:0.5 (m/m, mRNA to RNAi). Optionally, the PEG-KL4-mRNA complex is dried to form a powder formulation to deliver the wt p53 mRNA to lung cells as an aerosol.

Example 9

Delivery of the compositions of the invention into lung tissue is advantageous for treatment of respiratory disease, such as lung cancers. Hyperbranched poly (beta amino esters) are being developed to carry mRNAs, which could be inhaled by a patient in order to deliver the wild-type mRNAs to the patient's lung cells without accumulation of toxic effects. Research into poly(beta amino esters) indicates the molecules are an efficient means of delivering DNA and RNA into cells. (Patel, et al., Inhaled nanoformulated mRNA polyplexes for protein production in lung epithelium. Adv Mater. 2019 February; 31(8):e1805116; Zeng, et al., Efficient and robust highly branched poly(β-amino ester)/minicircle COL7A1 polymeric nanoparticles for gene delivery to recessive dystrophic epidermolysis bullosa keratinocytes. ACS Appl Mater Interfaces. 2019; 11:30661-30672; Anderson, et al., Structure/property studies of polymeric gene delivery using a library of poly(beta-amino esters). Mol Ther. 2005 March; 11(3):426-434).

Linear poly(beta amino esters) are prepared using a Michael addition of diacrylate to primary amine monomers. (Eltoukhy, et al., Degradable terpolymers with alkyl side chains demonstrate enhanced gene delivery potency and nanoparticle stability. Adv Mater. 2013 Mar. 13; 25(10):1487-1493; Kaczmarek, et al., Polymer-lipid nanoparticles for systemic delivery of mRNA to the lungs. Angew Chem Int Ed Engl. 2016 Oct. 24; 55(44):13808-13812; Zugates, et al., Rapid optimization of gene delivery by parallel end-modification of poly(beta-amino ester)s. Mol Ther. 2007 July; 15(7): 1306-1312). The polymers reaction results in polymers, which are then end-capped with a trifunctional amine, N-methyl 1,3 diaminopropane, to form different classes of poly(beta amino esters). (Gao & Yan, polyaddition of $B_2$ and $BB'_2$ type monomers to $A_2$ type monomer. 1. Synthesis of highly branched copoly(sulfone-amine)s. Macromolecules. 2001 Jan. 16; 34(2):156-161; Zeng, et al., Highly branched poly(β-amino ester)s for gene delivery in hereditary skin diseases. Advanced Drug Del Rev. 2021 September; 176:113842 Patel, et al., Inhaled nanoformulated mRNA polyplexes for protein production in lung epithelium. Adv Mater. 2019 February; 31(8):e1805116; Eltoukhy, et al., Effect of molecular weight of amine end-modified poly(β-aminoester)s on gene delivery efficiency and toxicity. Biomaterials. 2012 May; 33(13):3594-3603). The amines are used for addition of further polymers, resulting in hyperbranched polymers. (Zeng, et al., Highly branched poly(β-amino ester)s for gene delivery in hereditary skin diseases. Advanced Drug Del Rev. 2021 September; 176:113842; Patel, et al., Inhaled nanoformulated mRNA polyplexes for protein production in lung epithelium. Adv Mater. 2019 February; 31(8):e1805116)

The polymers are added to mRNA or a mixture of mRNA and RNA inhibitor(s), resulting in the hyperbranched poly (beta amino esters) condensing on the nucleic acids to form RNA-poly (beta amino esters) complexes that are biodegradable into nontoxic products. (Zeng, et al., Highly branched poly(β-amino ester)s for gene delivery in hereditary skin diseases. Advanced Drug Del Rev. 2021 September; 176:113842).

Functionalization of the polymers, by addition of receptor ligands like arginulglycylaspartic acid peptide (RGD) and epidermal growth factor (EGF), can be performed to increase cellular uptake of the complexes into cells. (Zeng, et al., Highly branched poly(β-amino ester)s for gene delivery in hereditary skin diseases. Advanced Drug Del Rev. 2021 September; 176:113842; Kunath, et al, Integrin targeting using RGD-PEI conjugates for in vitro gene transfer. J Gene Med. 2003:5:588-599; Schaffer & Lauffenburger, Optimization of cell surface binding enhances efficiency and specificity of molecular conjugates gene delivery. J Biol Chem. 1998; 273:28004-28009).

Example 10

Loading mRNA into a carrier molecule results in efficient in vivo treatment. (Kauffman, et al., Materials for non-viral intracellular delivery of messenger RNA therapeutics. J Control Release. 2016 Oct. 28; 240:227-234; Guan & Rosenecker, Nanotechnologies in delivery of mRNA therapeutics using nonviral vector-based delivery systems. Gene Ther. 2017 March; 24(3):133-143). Whereas naked mRNA is quickly degraded by extracellular RNases and is poorly uptaken by cells, the carriers described above show little to no immunogenicity, along with allowing rapid uptake and expression in the cytoplasm. (Kauffman, et al., Materials for non-viral intracellular delivery of messenger RNA therapeutics. J Control Release. 2016 Oct. 28; 240:227-234; Guan & Rosenecker, Nanotechnologies in delivery of mRNA therapeutics using nonviral vector-based delivery systems. Gene Ther. 2017 March; 24(3):133-143; Tsui, et al., Stability of endogenous and added RNA in blood specimens, serum, and plasma. Clin Chem. 2002 October; 48(10):1647-1653; Petsch, et al., Protective efficacy of in vitro synthesized, specific mRNA vaccines against influenza A virus infection. Nat Biotechnol. 2012 December; 30(12):1210-1216; Geall, et al., Nonviral delivery of self-amplifying RNA vaccines. Proc Nat Acad Sci USA. 2012 Sep. 4; 109(36):14604-14609; Pardi, et al., Zika virus protection by a single low-dose nucleoside-modified mRNA vaccination. Nature. 2017 Mar. 9; 543(7644):248-251). Further, development of RNA carrier molecules has resulted in non-toxic materials with clinical efficacy. (Pardi, et al., Expression kinetics of nucleoside-modified mRNA delivered in lipid nanoparticles to mice by various routes. J Control Release. 2015 Nov. 10; 217:345-351; Bahl, et al., Preclinical and clinical demonstration of immunogenicity by mRNA vaccines against H10N8 and H7N9 influenza viruses. Mol Ther. 2017 Jun. 7; 25(6): 1316-1327). Treatment of cancerous cells requires functioning cell checkpoint and repair machinery. To avoid the risk of additional genetic damage from genomic integration, which arises from viral introduction of DNA into the cell, the present invention uses mRNA introduction of wild-type p53 via microvesicle. This removes potential modifications of the host genome, which can accompany insertion of DNA into the host DNA. Further, as the mRNA is not integrated into the cell's DNA, further transmission is avoided, as the mRNA is not passed on to subsequent generations of cells. However, this requires the delivery be performed regularly to assure consistent expression of p53.

mRNA microvesicle complexes, described in Examples 3 through 5, are prepared and injected into a patient to reestablish functional, wild-type p53 in precancerous and cancerous cells. The mRNA-containing microvesicles are administered to a patient by either intratumoral injection or intraarterial or intravenous injection. The microvesicles bind to the target cell, using the target molecule, resulting in the vesicle fusing with the cell membrane and introducing the mRNA into the cytoplasm. Transport signals on the mRNA can transport the p53 mRNA to the endoplasmic reticulum for translation, thereby introducing wild-type p53 into the cell that results in cell growth arrest and cell senescence, or apoptosis.

Nanomicelles, a type of microvesicle, infused with modified mRNA, have been shown to be successfully injected into joints. (Aini, et al., Messenger RNA delivery of a cartilage-anabolic transcription factor as a disease-modifying strategy for osteoarthritis treatment. Scientific Reports. 2016 Jan. 5; 6:18743). Introduction of wild-type p53, or increased expression of wild-type p53, into precancerous or cancerous cells reactivates the cell maintenance pathways, allowing p53 to induce cell growth arrest, DNA repair, or apoptosis. Thus, the treatment either prevents the cancerous or precancerous cell from growing, as in the cell growth arrest and DNA repair arrest, or destroys the cell, as in apoptosis. By comparison, wild-type p53, introduction of the compositions into healthy cells will have little to no impact on cells that are not cancerous or precancerous as the compounds work the same as endogenous p53 in those cells.

In certain embodiments, the complex includes siRNA or shRNA inhibitors designed to bind to commonly-found p53 mutations in a target cancer, thereby triggering degradation of the mutated p53. As p53 exists as a tetramer molecule, such treatments eliminate the capability of the mutated p53 from acting as a functional wild-type RNA sponge resulting in loss of p53 function, i.e. forming a dominant negative phenotype.

Embodiments of the invention also provide for target molecules on the microvesicles, allowing the treatment to bind to glycoproteins on cancer cells to reduce potential side effects or lower efficacy of the treatment regimens. mRNA for wild-type p53, seen in Example 1, is suspended in an aqueous solution and a microvesicle is formed around the mRNA, as described in Examples 3 or 5, containing one or more targeting molecules, as provided in Example 4.

Example 11

Work has shown complexing plasmid DNA with polyethyleneimine (PEI) formed a complex that possessed little cytotoxicity, or effect on blood or liver function. (Kurosaki, et al., Ternary complexes of pDNA, polyethylenimine, and γ-polyglutamic acid for gene delivery systems. Biomaterials. 2009; 30: 2846-2853; Kurosaki, et al., Secure splenic delivery of plasmid DNA and its application to DNA vaccine. Biol Pharm Bull. 2013; 36:1800-1806). Research indicates that PEI compounds can be used to protect RNA, and show minimal toxicity in cells and organisms. (Hamada, et al., Anionic complex with efficient expression and good safety profile for mRNA delivery. Pharmaceutics. 2021 Jan. 19; 13(1):126).

Accordingly, mRNA is introduced directly into tissue, such as lung tissue, using PEI complexes, PEGylated synthetic KL4 peptide-mRNA complexes, or hyperbranched poly (beta amino esters), as described in Example 9. Upon formation of the mRNA-PEI complex, the compounds are inhalable to introduce the mRNA to the lungs. However, PEI is resistant to degradation, and thus with repeated doses the polymer could accumulate in the lung tissues and result in side effects.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments of a drug delivery system, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween.

What is claimed is:

1. A method of inducing cell senescence or apoptosis, comprising:
   contacting the cell with a composition comprising:
      a carrier, wherein the carrier is a microvesicle, polyplex nanomicelle, PEGylated synthetic KL4 peptide, hyperbranched poly (beta amino esters), or a mRNA-polyethylenimine complex;
      at least one ribonucleic acid in the carrier, wherein the at least one ribonucleic acid further comprises:
         a 5'-untranslated region of messenger ribonucleic acid selected from the group consisting of SEQ ID No. 1;
         a p53 messenger ribonucleic acid downstream of the 5'-untranslated region of messenger ribonucleic acid, wherein the p53 messenger ribonucleic acid is selected from the group consisting of SEQ ID No. 2, 3, or 4;
         a 3'-untranslated region of messenger ribonucleic acid downstream of the p53 messenger ribonucleic acid, wherein the 3'-untranslated region of messenger ribonucleic acid is selected from the group consisting of SEQ ID No. 5;
         a 3' poly A tail downstream of the 3'-untranslated region of messenger ribonucleic acid;
   wherein the cell is cancerous or precancerous; and
   wherein p53 in the cell has a loss of function mutation or a gain of function mutation.

2. The method of claim 1, wherein the carrier is a microvesicle having an interior space.

3. The method of claim 2, wherein the microvesicle is a niosome, liposome, or lipid nanoparticle.

4. The method of claim 1, wherein the carrier is polyethylene glycol-polyamino acid block copolymer-based polyplex nanomicelle.

5. The method of claim 1, wherein the carrier further comprises a targeting molecule on the surface of the carrier, wherein the targeting molecules is selected from the group consisting of alpha fetoprotein, anti-bladder tumor antigen, anti-BRCA1, anti-BRCA2, beta 2 microglobulin HRP, mucin 16, CD10, CD107a, CD13, CD 15, CD 19, CD 20, CD 22, CD 25, CD 117, CD138, CD146, CD147, CD227, CD318, CD326, CD66, CD56, carcinoembryonic antigen, chlorotoxin, epithelial tumor antigen, melanoma-associated antigen, cancer/testis antigen 1B, transferrin, somatostatin receptor ligand, arginulglycylaspartic acid peptide, epidermal growth factor, and combinations thereof.

6. The method of claim 1, wherein the 5'-untranslated region of messenger ribonucleic acid further comprises a 5' cap analog.

7. The method of claim 6, wherein the 5' cap analog is 7mG(5')ppp(5')N$_1$pNp.

8. The method of claim 1, further comprising administering the composition into a patient in need thereof, wherein the administering of the composition results in the cell contacting the composition.

9. The method of claim 8, wherein the composition is administered by aerosol administration, inhalation administration, intratumoral injection, intraarterial injection, or intravenous injection.

10. The method of claim 1, wherein the composition further comprises at least one interfering RNA directed against one or more p53 mutated mRNA molecules, selected from the group consisting of siRNA, shRNA, and a combination thereof.

11. The method of claim 10, wherein the at least one interfering RNA is siRNA or shRNA containing the sequence complementary to SEQ ID No. 6, 7, 8, 9, 10, 11, 12, 13, 14, 15, 16, 17, 18, 19, or combinations thereof.

12. A method of treating cancer or precancer in a patient, comprising the steps:
   administering a composition to a patient, wherein the composition comprises:
      a carrier, wherein the carrier is a microvesicle, polyplex nanomicelle, PEGylated synthetic KL4 peptide, hyperbranched poly (beta amino esters), or a mRNA-polyethylenimine complex;
      at least one ribonucleic acid in the carrier, wherein the at least one ribonucleic acid further comprises:
         a 5'-untranslated region of messenger ribonucleic acid selected from the group consisting of SEQ ID No. 1;
         a p53 messenger ribonucleic acid downstream of the 5'-untranslated region of messenger ribonucleic acid, wherein the p53 messenger ribonucleic acid is selected from the group consisting of SEQ ID No. 2, 3, or 4; and
         a 3'-untranslated region of messenger ribonucleic acid downstream of the p53 messenger ribonucleic acid, wherein the 3'-untranslated region of messenger ribonucleic acid is selected from the group consisting of SEQ ID No. 5;
         a 3' poly A tail downstream of the 3'-untranslated region of messenger ribonucleic acid;
   wherein the cancer or precancer has a loss of function mutation in the p53 protein or a gain of function mutation in the p53 protein.

13. The method of claim 12, wherein the carrier is a niosome, liposome, or lipid nanoparticle.

14. The method of claim 12, wherein the carrier is polyethylene glycol-polyamino acid block copolymer-based polyplex nanomicelle.

15. The method of claim 12, wherein the carrier further comprises a targeting molecule on the surface of the carrier, wherein the targeting molecules is selected from the group consisting of alpha fetoprotein, anti-bladder tumor antigen, anti-BRCA1, anti-BRCA2, beta 2 microglobulin HRP, mucin 16, CD10, CD107a, CD13, CD 15, CD 19, CD 20, CD 22, CD 25, CD 117, CD138, CD146, CD147, CD227, CD318, CD326, CD66, CD56, carcinoembryonic antigen, chlorotoxin, epithelial tumor antigen, melanoma-associated antigen, cancer/testis antigen 1B, transferrin, somatostatin receptor ligand, arginulglycylaspartic acid peptide, epidermal growth factor, and combinations thereof.

16. The method of claim 12, wherein the 5'-untranslated region of messenger ribonucleic acid further comprises a 5' cap analog.

17. The method of claim 16, wherein the 5' cap analog is 7mG(5')ppp(5')N$_1$pNp.

18. The method of claim 12, wherein the composition is administered by aerosol administration, inhalation administration, intratumoral injection, intraarterial injection, or intravenous injection.

19. The method of claim 12, wherein the composition further comprises at least one interfering RNA directed against one or more p53 mutated mRNA molecules, selected from the group consisting of siRNA, shRNA, and a combination thereof.

20. The method of claim 19, wherein the at least one interfering RNA is siRNA or shRNA containing the sequence complementary to SEQ ID No. 6, 7, 8, 9, 10, 11, 12, 13, 14, 15, 16, 17, 18, 19, or combinations thereof.

* * * * *

UNITED STATES PATENT AND TRADEMARK OFFICE
CERTIFICATE OF CORRECTION

| | | |
|---|---|---|
| PATENT NO. | : 11,491,177 B1 | Page 1 of 1 |
| APPLICATION NO. | : 17/513047 | |
| DATED | : November 8, 2022 | |
| INVENTOR(S) | : Lane Scheiber | |

It is certified that error appears in the above-identified patent and that said Letters Patent is hereby corrected as shown below:

In the Claims

On Column 39, Lines 39 to 45, after "the group consisting of", please insert --anti- -- before "alpha fetoprotein"; --anti- -- before "beta 2 microglobulin HRP"; --anti- -- before "mucin 16"; --anti- -- before "CD10"; --anti- -- before "CD107a"; --anti- -- before "CD13"; --anti- -- before "CD 15"; --anti- -- before "CD 19"; --anti- -- before "CD 20"; --anti- -- before "CD 22"; --anti- -- before "CD 25"; --anti- -- before "CD 117"; --anti- -- before "CD138"; --anti- -- before "CD146"; --anti- -- before "CD147"; --anti- -- before "CD227"; --anti- -- before "CD318"; --anti- -- before "CD326"; --anti- -- before "CD66"; --anti- -- before "CD56"; --anti- -- before "carcinoembryonic antigen"; --anti- -- before "epithelial tumor antigen"; --anti- -- before "melanoma-associated antigen"; --anti- -- before "cancer/testis antigen 1B"; and --anti- -- before "transferrin".

On Column 40, Lines 41 to 47, after "the group consisting of", please insert --anti- -- before "alpha fetoprotein"; --anti- -- before "beta 2 microglobulin HRP"; --anti- -- before "mucin 16"; --anti- -- before "CD10"; --anti- -- before "CD107a"; --anti- -- before "CD13"; --anti- -- before "CD 15"; --anti- -- before "CD 19"; --anti- -- before "CD 20"; --anti- -- before "CD 22"; --anti- -- before "CD 25"; --anti- -- before "CD 117"; --anti- -- before "CD138"; --anti- -- before "CD146"; --anti- -- before "CD147"; --anti- -- before "CD227"; --anti- -- before "CD318"; --anti- -- before "CD326"; --anti- -- before "CD66"; --anti- -- before "CD56"; --anti- -- before "carcinoembryonic antigen"; --anti- -- before "epithelial tumor antigen"; --anti- -- before "melanoma-associated antigen"; --anti- -- before "cancer/testis antigen 1B"; and --anti- -- before "transferrin".

Signed and Sealed this
Twenty-seventh Day of June, 2023

*Katherine Kelly Vidal*

Katherine Kelly Vidal
*Director of the United States Patent and Trademark Office*